United States Patent
Karin et al.

(12)

(10) Patent No.: US 6,268,194 B1
(45) Date of Patent: Jul. 31, 2001

(54) IKB KINASE AND METHODS OF USING SAME

(75) Inventors: Michael Karin; Joseph A. DiDonato, both of San Diego; David M. Rothwarf; Makio Hayakawa, both of La Jolla; Ebrahim Zandi, San Diego, all of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 08/810,131

(22) Filed: Feb. 25, 1997

(51) Int. Cl.$^7$ ............................. C12N 9/12; C12N 15/54
(52) U.S. Cl. ........................................ 435/194; 536/23.2
(58) Field of Search .................................. 435/194, 331; 536/23.2

(56) References Cited

PUBLICATIONS

Traenckner, E. B–M, et al. (1995) EMBO J. 14(2), 2876–2883.*
Davies, S.P., et al. (1994) Eur. J. Biochem. 223, 351–357.*
Affinity Chromatography, Principals & Methods, Pharmacia Fine Chemicals (1979) p. 6.*
Connelly and Marcu, "CHUK, a New Member of the Helix–Loop Helix and Leucine Zipper Families of Interacting Proteins, Contains a Serine–Threonine Kinase Catalytic Domain," *Cell. Mol. Biol. Res.* 41:537–549 (1995).
GenBank Accession #U12473; Locus MMU 12473 (1996).
GenBank Accession #U22512; Locus HSU 22512 (1996).
Verma et al., "Rel/NF–κB/IκB Family: Intimate Tales of Association and Dissociation," *Genes Devel.* 9:2723–2735 (1995).
Baeuerle and Baltimore, NF–κB: Ten Years After, *Cell* 87:13–20 (1996).
DiDonato et al., "Mapping of the Inducible IκB Phosphorylation Sites that Signal its Ubiquitination and Degradation," *Mol. Cell. Biol.* 16:1295–1304 (1996).
Chen et al., "Site–Specific Phosphorylation of IκBα by a Novel Ubiquitination–Dependent Protein Kinase Activity," *Cell* 84:853–862 (1996).
Lee et al., "Activation of the IκBα Kinase Complex by MEKK1, a Kinase of the JNK Pathway," *Cell* 88:213–222 (1997).

* cited by examiner

*Primary Examiner*—Charles L. Patterson, Jr.
(74) *Attorney, Agent, or Firm*—Medlen & Carroll, LLP

(57) ABSTRACT

The present invention provides a substantially purified nucleic acid molecule encoding a serine protein kinase (IκB kinase) that phosphorylates a protein (IκB) that inhibits the activity of the NF-κB transcription factor, vectors comprising such a nucleic acid molecule and host cells containing such vectors. In addition, the invention provides nucleotide sequences that can bind to a nucleic acid molecule of the invention, such nucleotide sequences being useful as probes or as antisense molecules. The invention also provides a substantially purified IκB kinase, which is a polypeptide that can phosphorylate an IκB protein, and peptide portions of the IκB kinase. In addition, the invention provides anti-IκB kinase antibodies, which specifically bind to an IκB kinase, and IκB kinase-binding fragments of such antibodies. The invention further provides methods of substantially purifying an IκB kinase, methods of identifying an agent that can alter the association of an IκB kinase with a second protein, and methods of identifying proteins that can interact with an IκB kinase.

8 Claims, 3 Drawing Sheets

```
                                            -35
                                TCGACGGAACCTGAGGCCGCTTGCCCTCCCGCCCC
1                                                                    60
atggagcggccccgggggctgcggccgggcgcgggcgggccctgggagatgcggagcgg
  M  E  R  P  P  G  L  R  P  G  A  G  G  P  W  E  M  R  E  R
61                                                                   120
ctgggcaccggcggcttcgggaacgtctgtctgtaccagcatcgggaacttgatctcaaa
  L  G  T  G  G  F  G  N  V  C  L  Y  Q  H  R  E  L  D  L  K
121                                                                  180
atagcaattaagtcttgtcgcctagagctaagtaccaaaaacagagaacgatggtgccat
  I  A  I  K  S  C  R  L  E  L  S  T  K  N  R  E  R  W  C  H
181                                                                  240
gaaatccagattatgaagaagttgaaccatgccaatgttgtaaaggcctgtgatgttcct
  E  I  Q  I  M  K  K  L  N  H  A  N  V  V  K  A  C  D  V  P
241                                                                  300
gaagaattgaatatttttgattcatgatgtgcctcttctagcaatggaatactgttctgga
  E  E  L  N  I  L  I  H  D  V  P  L  L  A  M  E  Y  C  S  G
301                                                                  360
ggagatctccgaaagctgctcaacaaaccagaaaattgttgtggacttaaagaaagccag
  G  D  L  R  K  L  L  N  K  P  E  N  C  C  G  L  K  E  S  Q
361                                                                  420
atactttctttactaagtgatatagggtctgggattcgatatttgcatgaaaacaaaatt
  I  L  S  L  L  S  D  I  G  S  G  I  R  Y  L  H  E  N  K  I
421                                                                  480
atacatcgagatctaaaacctgaaaacatagttcttcaggatgttggtggaaagataata
  I  H  R  D  L  K  P  E  N  I  V  L  Q  D  V  G  G  K  I  I
481                      (peptide 1)                                 540
cataaaataattgatctgggatatgccaaagatgttgatcaaggaagtctgtgtacatct
  H  K  I  I  D  L  G  Y  A  K  D  V  D  Q  G  S  L  C  T  S
541                                                                  600
tttgtgggaacactgcagtatctggccccagagctctttgagaataagccttacacagcc
  F  V  G  T  L  Q  Y  L  A  P  E  L  F  E  N  K  P  Y  T  A
601                                                                  660
actgttgattattggagctttgggaccatggtatttgaatgtattgctggatataggcct
  T  V  D  Y  W  S  F  G  T  M  V  F  E  C  I  A  G  Y  R  P
661                                                                  720
ttttttgcatcatctgcagccatttacctggcatgagaagattaagaagaaggatccaaag
  F  L  H  H  L  Q  P  F  T  W  H  E  K  I  K  K  K  D  P  K
721                                                                  780
tgtatatttgcatgtgaagagatgtcaggagaagttcggtttagtagccatttacctcaa
  C  I  F  A  C  E  E  M  S  G  E  V  R  F  S  S  H  L  P  Q
781                                                                  840
ccaaatagcctttgtagtttaatagtagaacccatggaaaactggctacagttgatgttg
  P  N  S  L  C  S  L  I  V  E  P  M  E  N  W  L  Q  L  M  L
841                                                                  900
aattgggaccctcagcagagaggaggacctgttgaccttactttgaagcagccaagatgt
  N  W  D  P  Q  Q  R  G  G  P  V  D  L  T  L  K  Q  P  R  C
901                                                                  960
tttgtattaatggatcacatttttgaatttgaagatagtacacatcctaaatatgacttct
  F  V  L  M  D  H  I  L  N  L  K  I  V  H  I  L  N  M  T  S
961                                                                 1020
```

FIG. 1A

```
gcaaagataatttcttttctgttaccacctgatgaaagtcttcattcactacagtctcgt
 A  K  I  I  S  F  L  L  P  P  D  E  S  L  H  S  L  Q  S  R
1021                                                      1080
attgagcgtgaaactggaataaatactggttctcaagaacttctttcagagacaggaatt
 I  E  R  E  T  G  I  N  T  G  S  Q  E  L  L  S  E  T  G  I
1081                                                      1140
tctctggatcctcggaaaccagcctctcaatgtgttctagatggagttagaggctgtgat
 S  L  D  P  R  K  P  A  S  Q  C  V  L  D  G  V  R  G  C  D
1141                                                      1200
agctatatggtttatttgtttgataaaagtaaaactgtatatgaagggccatttgcttcc
 S  Y  M  V  Y  L  F  D  K  S  K  T  V  Y  E  G  P  F  A  S
1201                                                      1260
agaagtttatctgattgtgtaaattatattgtacaggacagcaaaatacagcttccaatt
 R  S  L  S  D  C  V  N  Y  I  V  Q  D  S  K  I  Q  L  P  I
1261                                                      1320
atacagctgcgtaaagtgtgggctgaagcagtgcactatgtgtctggactaaaagaagac
 I  Q  L  R  K  V  W  A  E  A  V  H  Y  V  S  G  L  K  E  D
1321                                                      1380
tatagcaggctcttttcagggacaaagggcagcaatgttaagtcttcttagatataatgct
 Y  S  R  L  F  Q  G  Q  R  A  A  M  L  S  L  L  R  Y  N  A
1381                                                      1440
aacttaacaaaaatgaagaacactttgatctcagcatcacaacaactgaaagctaaattg
 N  L  T  K  M  K  N  T  L  I  S  A  S  Q  Q  L  K  A  K  L
1441                                                      1500
gagttttttcacaaaagcattcagcttgacttggagagatacagcgagcagatgacgtat
 E  F  F  H  K  S  I  Q  L  D  L  E  R  Y  S  E  Q  M  T  Y
1501                                                      1560
gggatatcttcagaaaaaatgctaaaagcatggaaagaaatggaagaaaaggccatccac
 G  I  S  S  E  K  M  L  K  A  W  K  E  M  E  E  K  A  I  H
1561                                                      1620
tatgctgaggttggtgtcattggatacctggaggatcagattatgtctttgcatgctgaa
 Y  A  E  V  G  V  I  G  Y  L  E  D  Q  I  M  S  L  H  A  E
1621                                                      1680
atcatggagctacagaagagcccctatggaagacgtcagggagacttgatggaatctctg
 I  M  E  L  Q  K  S  P  Y  G  R  R  Q  G  D  L  M  E  S  L
1681                                                      1740
gaacagcgtgccattgatctatataagcagttaaaacacagaccttcagatcactcctac
 E  Q  R  A  I  D  L  Y  K  Q  L  K  H  R  P  S  D  H  S  Y
1741                                                      1800
agtgacagcacagagatggtgaaaatcattgtgcacactgtgcagagtcaggaccgtgtg
 S  D  S  T  E  M  V  K  I  I  V  H  T  V  Q  S  Q  D  R  V
1801                                                      1860
ctcaaggagcgttttggtcatttgagcaagttgttgggctgtaagcagaagattattgat
 L  K  E  R  F  G  H  L  S  K  L  L  G  C  K  Q  <u>K  I  I  D</u>
1861                                        (peptide 2) 1920
ctactccctaaggtggaagtggccctcagtaatatcaaagaagctgacaatactgtcatg
 <u>L  L  P</u>  K  V  E  V  A  L  S  N  I  K  E  A  D  N  T  V  M
1921                                                      1980
ttcatgcagggaaaaaggcagaaagaaatatggcatctccttaaaattgcctgtacacag
 F  M  Q  G  K  R  Q  K  E  I  W  H  L  L  K  I  A  C  T  Q
1981                                                      2040
agttctgcccgctctcttgtaggatccagtctagaaggtgcagtaacccctcaagcatac
 S  S  A  R  S  L  V  G  S  S  L  E  G  A  V  T  P  Q  A  Y
```

FIG. 1B

```
2041                                                         2100
gcatggctggcccccgacttagcagaacatgatcattctctgtcatgtgtggtaactcct
 A  W  L  A  P  D  L  A  E  H  D  H  S  L  S  C  V  V  T  P
2101                                                         2160
caagatggggagacttcagcacaaatgatagaagaaaatttgaactgccttggccattta
 Q  D  G  E  T  S  A  Q  M  I  E  E  N  L  N  C  L  G  H  L
2161                                                         2220
agcactattattcatgaggcaaatgaggaacagggcaatagtatgatgaatcttgattgg
 S  T  I  I  H  E  A  N  E  E  Q  G  N  S  M  M  N  L  D  W agttggttaacagaatga
 S  W  L  T  E  *
2221           2238
```

FIG. 1C

IKB KINASE AND METHODS OF USING SAME

This invention was made with government support under grant number CA50528 awarded by the National Institutes of Health. The government has certain rights in the invention.

BACKGROUND OF THE INVENTION

1. Field of the Invention

The present invention relates generally to molecular biology and biochemistry and more specifically to a protein kinase, IκB kinase, which is activated in response to environmental stresses and proinflammatory signals to phosphorylate inhibitors of the NF-κB transcription factors and to methods of using the protein kinase.

2. Background Information

The induction of gene expression due to exposure of a cell to a specific stimulus is a tightly controlled process. Depending on the inducing stimulus, it can be critical to survival of the cell that one or more genes be rapidly induced, such that the expressed gene product can mediate its effect. For example, an inflammatory response stimulated due to an injury to or infection of a tissue results in rapid vasodilation in the area of the injury and infiltration of effector cells such as macrophages. Vasodilation occurs within minutes of the response and is due, in part, to the expression of cytokines in the injured region.

The rapid induction, for example, of an inflammatory response or an immune response, requires that the transcription factors involved in regulating such responses be present in the cell in a form that is amenable to rapid activation. Thus, upon exposure to an inducing stimulus, the response can occur quickly. If, on the other hand, such transcription factors were not already present in a cell in an inactive state, the factors first would have to be synthesized upon exposure to an inducing stimulus, greatly reducing the speed with which a response such as an inflammatory response could occur.

Regulation of the activity of transcription factors involved in such rapid induction of gene expression can occur by various mechanisms. For example, in some cases, a transcription factor that exists in an inactive state in a cell can be activated by a post-translational modification such as phosphorylation on one or more serine, threonine or tyrosine residues. In addition, a transcription factor can be inactive due to an association with a regulatory factor, which, upon exposure to an inducing stimulus, is released from the transcription factor, thereby activating the transcription factor. Alternatively, an inactive transcription factor may have to associate with a second protein in order to have transcriptional activity.

Rarely, as in the case of glucocorticoids, the inducing stimulus interacts directly with the inactive transcription factor, rendering it active and resulting in the induction of gene expression. More often, however, an inducing stimulus initiates the induced response by interacting with a specific receptor present on the cell membrane or by entering the cell and interacting with an intracellular protein. Furthermore, the signal generally is transmitted along a pathway, for example, from the cell membrane to the nucleus, due to a series of interactions of proteins. Such signal transduction pathways allow for the rapid transmission of an extracellular inducing stimulus such that the appropriate gene expression is rapidly induced.

Although the existence of signal transduction pathways has long been recognized and many of the cellular factors involved in such pathways have been described, the pathways responsible for the expression of many critical responses, including the inflammatory response and immune response, have not been completely defined. For example, it is recognized that various inducing stimuli such as bacteria or viruses activate common arms of the immune and inflammatory responses. However, differences in the gene products expressed also are observed, indicating that these stimuli share certain signal transduction pathways but also induce other pathways unique to the inducing stimulus. Furthermore, since inducing agents such as bacteria or viruses initially stimulate different signal transduction pathways, yet induce the expression of common genes, some signal transduction pathways must converge at a point such that the different pathways activate common transcription factors.

A clearer understanding of the proteins involved in such pathways can allow a description, for example, of the mechanism of action of a drug that is known to interfere with the expression of genes regulated by a particular pathway, but the target of which is not known. In addition, the understanding of such pathways can allow the identification of a defect in the pathway that is associated with a disease such as cancer. For example, the altered expression of cell adhesion molecules is associated with the ability of a cancer cell to metastasize. However, the critical proteins involved in the signal transduction pathway leading to expression of cell adhesion molecules have not been identified. Thus, a need exists to identify the proteins involved in signal transduction pathways, particularly those proteins present at the convergence point of different initial pathways that result in the induction, for example, of gene products involved in the inflammatory and immune responses. The present invention satisfies this need and provides related advantages as well.

SUMMARY OF THE INVENTION

The present invention provides a substantially purified nucleic acid molecule encoding a full length human serine protein kinase (IκB kinase), which is activated in response to proinflammatory signals to phosphorylate a protein (IκB) that inhibits the activity of the NF-κB transcription factor. For example, the invention provides the nucleic acid molecule having the nucleotide sequence shown as SEQ ID NO: 1, which encodes a cytokine inducible IκB kinase, and a nucleotide sequence complementary to that shown in SEQ ID NO: 1, particularly the sequence shown as nucleotides 1 to 128 in SEQ ID NO: 1. The invention also provides vectors comprising a nucleic acid molecule of the invention and host cells containing such vectors. In addition, the invention provides nucleotide sequences that bind to a nucleic acid molecule of the invention, including to nucleotides 1 to 128 as shown in SEQ ID NO: 1. Such nucleotide sequences of the invention are useful as probes, which can be used to identify the presence of a nucleic acid molecule encoding an IκB kinase in a sample, and as antisense molecules, which can be used to inhibit the expression of a nucleic acid molecule encoding an IκB kinase.

The present invention also provides a substantially purified full length human IκB kinase, which can phosphorylate an IκB protein. For example, the invention provides a polypeptide having the amino acid sequence shown as SEQ ID NO: 2, particularly the amino acid sequence comprising amino acids 1 to 31 at the N-terminus of the polypeptide of SEQ ID NO: 2. The invention also provides peptide portions of an IκB kinase, particularly peptide portions comprising one or more contiguous amino acids of the N-terminal amino acids shown as residues 1 to 31 in SEQ ID NO: 2. A peptide portion of an IκB kinase can comprise the kinase domain of the IκB kinase or can comprise a peptide useful for eliciting production of an antibody that specifically binds to an IκB kinase. Accordingly, the invention also provides anti-IκB kinase antibodies that specifically bind to an IκB kinase, particularly to an epitope comprising at least one of the amino acids shown as residues 1 to 31 of SEQ ID NO: 2, and also provides IκB kinase-binding fragments of such antibodies. In addition, the invention provides cell lines producing anti-IκB kinase antibodies or IκB kinase-binding fragments thereof.

The present invention further provides methods of substantially purifying an IκB kinase, as well as methods of identifying an agent that can alter the association of an IκB kinase with a second protein that associates with an IκB kinase in vitro or in vivo. Such a second protein can be, for example, an IκB protein, which is a substrate for IκB kinase activity and is downstream of the IκB kinase in a signal transduction pathway that results in the regulated expression of a gene; a protein that is upstream of the IκB kinase in a signal transduction pathway and regulates the kinase activity of the IκB kinase; or a protein that acts as a regulatory subunit of the IκB kinase polypeptide. An agent that alters the association of an IκB kinase with a second protein can be, for example, a peptide, a polypeptide, a peptidomimetic or an organic molecule. Such agents can be useful for modulating the level of phosphorylation of IκB in a cell, thereby modulating the activity of NF-κB in the cell and the expression of a gene regulated by NF-κB.

The invention also provides methods of identifying proteins that can interact with an IκB kinase, such proteins which can be a downstream effector of the IκB kinase such as a member of the IκB family of proteins or an upstream activator or a regulatory subunit of the IκB kinase. Such proteins that interact with an IκB kinase can be isolated, for example, by coprecipitation with the IκB kinase or by using the kinase as a ligand, and can be involved, for example, in tissue specific regulation of NF-κB activation and consequent tissue specific gene expression.

BRIEF DESCRIPTION OF THE DRAWING

FIG. 1 shows a nucleotide sequence (SEQ ID NO: 1; lower case letter) and deduced amino acid sequence (SEQ ID NO: 2; upper case letters) of a full length human IκB kinase. Nucleotide positions are indicated, where the "A" of the ATG encoding the initiator methionine is position 1. Underlined amino acid residues indicate the peptide portions of the protein ("peptide 1" and "peptide 2") that were sequenced and used to design oligonucleotide probes. The asterisk indicates the sequence encoding the STOP codon.

DETAILED DESCRIPTION OF THE INVENTION

The present invention provides a substantially purified nucleic acid molecule encoding a full length human serine protein kinase (IκB kinase) that is activated in response to proinflammatory signals and phosphorylates proteins (IκB's), which can bind to and inhibit the activity of NF-κB transcription factors. For example, the invention provides a substantially purified nucleotide sequence (SEQ ID NO: 1) encoding a full length human IκB kinase having the amino acid sequence shown as SEQ ID NO: 2 (see FIG. 1).

As used herein, the term "substantially purified," when used in reference to a nucleic acid molecule of the invention, means that the nucleic acid molecule is relatively free from contaminating lipids, proteins, nucleic acids or other cellular material normally associated with a nucleic acid molecule in a cell. A substantially purified nucleic acid molecule of the invention can be obtained, for example, by chemical synthesis of the nucleotide sequence shown as SEQ ID NO: 1 or by cloning the molecule using methods such as those disclosed in Example II.

Nucleic acid molecules related to that shown in SEQ ID NO: 1 previously have been described (Connelly and Marcu, *Cell. Mol. Biol. Res*. 41:537–549 (1995), which is incorporated herein by reference). For example, Connelly and Marcu describe a 3466 base pair (bp) nucleic acid molecule (GenBank Accession #U12473; Locus MMU 12473), which is incorporated herein by reference), which encodes a full length mouse polypeptide having an apparent molecular mass of 85 kiloDaltons (kDa). A 2146 bp nucleic acid molecule (GenBank Accession #U22512; Locus HSU 22512), which is incorporated herein by reference), which encodes a portion of the polypeptide shown in SEQ ID NO: 2 also was described. However, the amino acid sequence deduced from #U22512 lacks amino acids 1 to 31 as shown in SEQ ID NO: 2 and, therefore, is not a full length protein. The polypeptides encoded by the nucleotide sequences of GenBank Accession #U12473 and #U22512 share about 95% identity at the amino acid level and are substantially similar to that shown in SEQ ID NO: 2. No function has been demonstrated for these polypeptides.

A nucleic acid molecule of the invention is exemplified by the nucleotide sequence shown as SEQ ID NO: 1, which encodes a full length, human IκB kinase (SEQ ID NO: 2; FIG. 1), the activity of which is stimulated by a cytokine or other proinflammatory signal. Due to the degeneracy of the genetic code and in view of the disclosed amino acid sequence of a full length human IκB kinase (SEQ ID NO: 2), additional nucleic acid molecules of the invention would be well known to those skilled in the art. Such nucleic acid molecules have a nucleotide sequence that is different from SEQ ID NO: 1 but, nevertheless, encode the amino acid sequence shown as SEQ ID NO: 2. Thus, the invention provides a nucleic acid molecule comprising a nucleotide sequence encoding the amino acid sequence of a full length human IκB kinase as shown in SEQ ID NO: 2.

As used herein, reference to "a nucleic acid molecule encoding an IκB kinase" indicates 1) the polynucleotide sequence of one strand of a double stranded DNA molecule comprising the nucleotide sequence that codes for an IκB kinase and can be transcribed into an RNA that encodes the kinase, or 2) an RNA molecule, which can be translated into an IκB kinase. It is recognized that a double stranded DNA molecule also comprises a second polynucleotide strand that is complementary to the coding strand and that the disclosure of a polynucleotide sequence comprising a coding sequence necessarily discloses the complementary polynucleotide sequence. Accordingly, the invention provides polynucleotide sequences, including, for example, polydeoxyribonucleotide or polyribonucleotide sequences that are complementary to the nucleotide sequence shown as SEQ ID NO: 1 or to a nucleic acid molecule encoding a human IκB kinase having the amino acid sequence shown as SEQ ID NO: 2.

As used herein, the term "polynucleotide" is used in its broadest sense to mean two or more nucleotides or nucleotide analogs linked by a covalent bond. The term "oligonucleotide" also is used herein to mean two or more nucleotides or nucleotide analogs linked by a covalent bond, although those in the art will recognize that oligonucleotides generally are less than about fifty nucleotides in length and, therefore, are a subset within the broader meaning of the term "polynucleotide."

In general, the nucleotides comprising a polynucleotide are naturally occurring deoxyribonucleotides, such as adenine, cytosine, guanine or thymine linked to 2'-deoxyribose, or ribonucleotides such as adenine, cytosine, guanine or uracil linked to ribose. However, a polynucleotide also can comprise nucleotide analogs, including non-naturally occurring synthetic nucleotides or modified naturally occurring nucleotides. Such nucleotide analogs are well known in the art and commercially available, as are polynucleotides containing such nucleotide analogs (Lin et al., *Nucl. Acids Res.* 22:5220–5234 (1994); Jellinek et al., *Biochemistry* 34:11363–11372 (1995); Pagratis et al., *Nature Biotechnol.* 15:68–73 (1997)). The covalent bond linking the nucleotides of a polynucleotide generally is a phosphodiester bond. However, the covalent bond also can be any of numerous other bonds, including a thiodiester bond, a phosphorothioate bond, a peptide-like bond or any other bond known to those in the art as useful for linking nucleotides to produce synthetic polynucleotides (see, for example, Tam et al., *Nucl. Acids Res.* 22:977–986 (1994); Ecker and Crooke, *BioTechnology* 13:351360 (1995)).

Where it is desired to synthesize a polynucleotide of the invention, the artisan will know that the selection of particular nucleotides or nucleotide analogs and the covalent bond used to link the nucleotides will depend, in part, on the purpose for which the polynucleotide is prepared. For example, where a polynucleotide will be exposed to an environment containing substantial nuclease activity, the artisan will select nucleotide analogs or covalent bonds that are relatively resistant to the nucleases. A polynucleotide comprising naturally occurring nucleotides and phosphodiester bonds can be chemically synthesized or can be produced using recombinant DNA methods, using an appropriate polynucleotide as a template. In comparison, a polynucleotide comprising nucleotide analogs or covalent bonds other than phosphodiester bonds generally will be chemically synthesized, although an enzyme such as T7 polymerase can incorporate certain types of nucleotide analogs and, therefore, can be used to produce such a polynucleotide recombinantly from an appropriate template Jellinek et al., supra, 1995).

The invention also provides nucleotide sequences that can bind to a nucleic acid molecule of the invention. Such nucleotide sequences are useful, for example, as probes, which can hybridize to a nucleic acid molecule encoding an IκB kinase and allow the identification of the nucleic acid molecule in a sample. A nucleotide sequence of the invention is characterized, in part, in that it is at least nine nucleotides in length, such sequences being particularly useful as primers for the polymerase chain reaction (PCR), and can be at least fourteen nucleotides in length or, if desired, at least seventeen nucleotides in length, such nucleotide sequences being particularly useful as hybridization probes, although such sequences also can be used for PCR. In addition, a nucleotide sequence of the invention comprises at least six nucleotides 5' to nucleotide position 92 as shown in SEQ ID NO: 1 (FIG. 1), preferably at least nine nucleotides 5' to position 92, or more as desired, where SEQ ID NO: 1 is shown in the conventional manner from the 5'-terminus (FIG. 1; upper left) to the 3'-terminus.

A nucleic acid molecule encoding an IκB kinase such as the nucleotide sequence shown in SEQ ID NO: 1 diverges from the sequence encoding the mouse homolog (GenBank Accession #U12473) in the region encoding amino acid 30. Thus, a nucleotide sequence comprising nucleotides 123 to 125 as shown in SEQ ID NO: 1, which encodes amino acid 30 of a human IκB kinase, can be particularly useful, for example, for identifying the presence of a nucleic acid molecule encoding a human IκB kinase in a sample.

A nucleotide sequence of the invention can comprise a portion of a coding sequence of a nucleic acid molecule encoding an IκB kinase or of a sequence complementary thereto, depending on the purpose for which the nucleotide sequence is to be used. In addition, a mixture of a coding sequence and its complementary sequence can be prepared and, if desired, can be allowed to anneal to produce double stranded oligonucleotides.

The invention also provides antisense nucleic acid molecules, which are complementary to a nucleic acid molecule encoding a human IκB kinase and can bind to and inhibit the expression of the nucleic acid molecule. As disclosed herein, expression of an antisense molecule complementary to the nucleotide sequence shown in SEQ ID NO: 1 inhibited the cytokine inducible expression of an NF-κB dependent reporter gene in a cell (see Example II). Thus, an antisense molecule of the invention can be useful for decreasing IκB kinase activity in a cell, thereby reducing or inhibiting the level of NF-κB mediated gene expression. These experiments were performed twenty-four hours after the cells were transfected (Example II). Expression of the antisense molecule in the cell also resulted in a decreased level of IκB kinase activity as compared to vector transfected control cells, indicating that the IκB kinase has a relatively short half life.

An antisense nucleic acid molecule of the invention can comprise a sequence complementary to entire coding sequence of an IκB kinase such as sequence complementary to SEQ ID NO: 1. In addition, a nucleotide sequence complementary to a portion of a nucleic acid molecule encoding an IκB kinase can be useful as an antisense molecule, particularly a nucleotide sequence complementary to nucleotides 1 to 128 of SEQ ID NO: 1 or, for example, a nucleotide sequence comprising at least 9 nucleotides on each side of the ATG encoding the initiator methionine (complementary to positions –9 to 12 of SEQ ID NO: 1) or, if desired, at least 17 nucleotides on each side of the ATG codon (complementary to positions –17 to 20 of SEQ ID NO: 1).

Antisense methods involve introducing the nucleic acid molecule, which is complementary to and can hybridize to the target nucleic acid molecule, into a cell. An antisense nucleic acid molecule can be a chemically synthesized polynucleotide, which can be introduced into the target cells by methods of transfection, or can be expressed from a plasmid or viral vector, which can be introduced into the cell and stably or transiently expressed using well known methods (see, for example, Sambrook et al., *Molecular Cloning: A laboratory manual* (Cold Spring Harbor Laboratory Press 1989); Ausubel et al., *Current Protocols in Molecular Biology* (Green Publ., NY 1989), each of which is incorporated herein by reference). One in the art would know that the ability of an antisense nucleic acid molecule to hybridize to the target nucleic acid sequence depends, for example, on the degree of complementarity shared between the sequences, the GC content of the hybridizing molecules, and the length of the antisense nucleic acid sequence, which can be at least ten nucleotides in length, generally at least thirty nucleotides in length or at least fifty nucleotides in length, and can be up to the full length of a nucleotide sequence encoding the IκB kinase as shown in SEQ ID NO: 2 (see Sambrook et al., supra, 1989).

The invention also provides vectors comprising a nucleic acid molecule of the invention and host cells, which are appropriate for maintaining such vectors. Vectors, which can be cloning vectors or expression vectors, are well known in the art and commercially available. An expression vector comprising a nucleic acid molecule of the invention, which can encode an IκB kinase or can be an antisense molecule, can be used to express the nucleic acid molecule in a cell.

In general, an expression vector contains the expression elements necessary to achieve, for example, sustained transcription of the nucleic acid molecule, although such elements also can be inherent to the nucleic acid molecule cloned into the vector. In particular, an expression vector contains or encodes a promoter sequence, which can provide constitutive or, if desired, inducible expression of a cloned nucleic acid sequence, a poly-A recognition sequence, and a ribosome recognition site, and can contain other regulatory elements such as an enhancer, which can be tissue specific. The vector also contains elements required for replication in a procaryotic or eukaryotic host system or both, as desired. Such vectors, which include plasmid vectors and viral vectors such as bacteriophage, baculovirus, retrovirus, lentivirus, adenovirus, vaccinia virus, semliki forest virus and adeno-associated virus vectors, are well known and can be purchased from a commercial source (Promega, Madison Wis.; Stratagene, La Jolla Calif.; GIBCO/BRL, Gaithersburg Md.) or can be constructed by one skilled in the art (see, for example, *Meth. Enzymol.*, Vol. 185, D. V. Goeddel, ed. (Academic Press, Inc., 1990); Jolly, *Canc. Gene Ther.* 1:51–64 (1994); Flotte, *J. Bioenerg. Biomemb.* 25:37–42 (1993); Kirshenbaum et al., *J. Clin. Invest* 92:381–387 (1993), which is incorporated herein by reference).

A nucleic acid molecule, including a vector, can be introduced into a cell by any of a variety of methods known in the art (Sambrook et al., supra, 1989, and in Ausubel et al., *Current Protocols in Molecular Biology*, John Wiley and Sons, Baltimore, Md. (1994), which is incorporated herein by reference). Such methods include, for example, transfection, lipofection, microinjection, electroporation and infection with recombinant vectors or the use of liposomes.

Introduction of a nucleic acid molecule by infection with a viral vector is particularly advantageous in that it can efficiently introduce the nucleic acid molecule in to a cell ex vivo or in vivo. Moreover, viruses are very specialized and typically infect and propagate in specific cell types. Thus, their natural specificity can be used to target the nucleic acid molecule contained in the vector to specific cell types. For example, a vector based on HIV-1 can be used to target an antisense IκB kinase molecule to HIV-1 infected cells, thereby reducing the phosphorylation of IκB, which can decrease the high level of constitutive NF-κB activity present in HIV-1 infected cells. Viral or non-viral vectors also can be modified with specific receptors or ligands to alter target specificity through receptor mediated events.

A nucleic acid molecule also can be introduced into a cell using methods that do not require the initial introduction of the nucleic acid molecule into a vector. For example, a nucleic acid molecule encoding an IκB kinase can be introduced into a cell using a cationic liposomes, which also can be modified with specific receptors or ligands as described above (Morishita et al., *J. Clin. Invest.*, 91:2580–2585 (1993), which is incorporated herein by reference; see, also, Nabel et al., supra, 1993)). In addition, a nucleic acid molecule can be introduced into a cell using, for example, adenovirus-polylysine DNA complexes (see, for example, Michael et al., *J. Biol. Chem.*, 268:6866–6869 (1993), which is incorporated herein by reference). Other methods of introducing a nucleic acid molecule into a cell such that the encoded IκB kinase or antisense nucleic acid molecule can be expressed are well known (see, for example, Goeddel, supra, 1990).

Selectable marker genes encoding, for example, a polypeptide conferring neomycin resistance (Neo$^R$) also are readily available and, when linked to a nucleic acid molecule of the invention or incorporated into a vector containing the nucleic acid molecule, allows for the selection of cells that have incorporated the nucleic acid molecule. Other selectable markers such as that conferring hygromycin, puromycin or ZEOCIN (Invitrogen) resistance are known to those in the art of gene transfer can be used to identify cells containing the nucleic acid molecule, including the selectable marker gene.

A "suicide" gene also can be incorporated into a vector so as to allow for selective inducible killing of a cell containing the gene. A gene such as the herpes simplex virus thymidine kinase gene (TK) can be used as a suicide gene to provide for inducible destruction of such cells. For example, where it is desired to terminate the expression of an introduced nucleic acid molecule encoding IκBor an antisense IκBmolecule in cells containing the nucleic acid molecule, the cells can be exposed to a drug such as acyclovir or gancyclovir, which can be administered to an individual.

Numerous methods are available for transferring nucleic acid molecules into cultured cells, including the methods described above. In addition, a useful method can be similar to that employed in previous human gene transfer studies, where tumor infiltrating lymphocytes (TILs) were modified by retroviral gene transduction and administered to cancer patients (Rosenberg et al., *New Engl. J. Med.* 323:570–578 (1990)). In that Phase I safety study of retroviral mediated gene transfer, TILs were genetically modified to express the Neomycin resistance (Neo$^R$) gene. Following intravenous infusion, polymerase chain reaction analyses consistently found genetically modified cells in the circulation for as long as two months after administration. No infectious retroviruses were identified in these patients and no side effects due to gene transfer were noted in any patients. These retroviral vectors have been altered to prevent viral replication by the deletion of viral gag, pol and env genes. Such a method can also be used ex vivo to transduce cells taken from a subject (see Anderson et al., U.S. Pat. No. 5,399,346, issued Mar. 21, 1995, which is incorporated herein by reference).

When retroviruses are used for gene transfer, replication competent retroviruses theoretically can develop due to recombination of retroviral vector and viral gene sequences in the packaging cell line utilized to produce the retroviral vector. Packaging cell lines in which the production of replication competent virus by recombination has been reduced or eliminated can be used to minimize the likelihood that a replication competent retrovirus will be produced. Hence, all retroviral vector supernatants used to infect cells will be screened for replication competent virus by standard assays such as PCR and reverse transcriptase assays.

To function properly, a cell requires the precise regulation of expression of nearly all genes. Such gene regulation is accomplished by activation or repression of transcription by various transcription factors, which interact directly with regulatory sequences on nuclear DNA. The ability of transcription factors to bind DNA or activate or repress transcription is regulated in response to external stimuli. In the case of the transcription factor NF-κB, critical factors involved in the signaling pathway mediating its activation have not been identified (Verma, et al., *Genes Devel.* 9:2723–2735 (1995); Baeuerle and Baltimore, *Cell* 87:13–20 (1996)).

NF-κB is a member of the Rel family of transcription factors, which are present in most if not all animal cells (Thanos and Maniatis, *Cell* 80:629–532 (1995)). Rel proteins, which include, for example, RelA (p65), c-Rel, p50, p52 and the Drosophila dorsal and Dif gene products, are characterized by region of about 300 amino acids sharing approximately 35% to 61% homology ("Rel homology domain"). The Rel homology domain includes DNA binding and dimerization domains and a nuclear localization signal. Rel proteins are grouped into one of two classes, depending on whether the protein also contains a transcriptional activation domain (Siebenlist et al., *Ann. Rev. Cell Biol.* 10:405–455 (1994)).

Rel proteins can form homodimers or heterodimers, which can be transcriptionally activating depending on the presence of a transactivation domain. The most common Rel/NF-κB dimer, which is designated "NF-κB," is a p50/p65 heterodimer that can activate transcription of genes containing the appropriate κB binding sites. p50/p65 NF-κB is present in most cell types and is considered the prototype of the Rel/NF-κB family of transcription factors. Different dimers vary in their binding to different κB elements, kinetics of nuclear translocation and levels of expression in a tissue (Siebenlist et al., supra, 1994). As used herein, the term "Rel/NF-κB" is used to refer generally to the Rel family of transcription factors, and the term "NF-κB" is used to refer specifically to the Rel/NF-κB factor consisting of a p50/p65 heterodimer.

NF-κB originally was identified by its ability to bind a specific DNA sequence present in the immunoglobulin κ light chain gene enhancer, the "κB element" (Sen and Baltimore, *Cell* 46:705–709 (1986)). The κB element has been identified in numerous cellular and viral promoters, including promoters present in human immunodeficiency virus-1 (HIV-1); immunoglobulin superfamily genes such as the MHC class 1 (H-2κ) gene; cytokine genes such as the tumor necrosis factor α (TNFα), interleukin-1β (IL-1β), IL-2, IL-6 and the granulocyte-macrophage colony stimulating factor (GM-CSF) gene; chemokine genes such as RANTES and IL-8; and cell adhesion protein genes such as E-selectin. The κB element exhibits dyad symmetry and each half site of the element likely is bound by one subunit of an NF-κB dimer.

In the absence of an appropriate signaling stimulus, a Rel/NF-κB is maintained in the cytoplasm in an inactive form complexed with an IκB protein. Rel/NF-κB transcriptional activity is induced by numerous pathogenic events or stresses, including cytokines, chemokines, viruses and viral products, double stranded RNA, bacteria and bacterial products such as lipopolysaccharide (LPS) and toxic shock syndrome toxin-1, mitogens such as phorbol esters, physical and oxidative stresses, and chemical agents such as okadaic acid and cycloheximide (Thanos and Maniatis, supra, 1995; Siebenlist et al., supra, 1994). Significantly, the expression of genes encoding agents such as TNFα, IL-1, IL-6, interferon-β and various chemokines, which induce NF-κB activity, are, themselves, induced by NF-κB, resulting in amplification of their signal by a positive, self-regulatory loop (Siebenlist et al., supra, 1994). Phorbol esters, which activate T cells, also activate NF-κB and immunosuppressants such as cyclosporin A inhibit activation of T cells through T cell receptor mediated signals (Baldwin, *Ann. Rev. Immunol.* 14:649–681 (1996), which is incorporated herein by reference).

Regulation of specific genes by NF-κB can require interaction of NF-κB with one or more other DNA binding proteins. For example, expression of E-selectin requires an interaction of NF-κB, the bZIP protein ATF-2 and HMG-I (Y), and expression of the IL-2 receptor α gene requires an interaction of NF-κB, HMG-I(Y) and the ets-like protein, ELF-1 (Baldwin, supra, 1996).

The numerous agents that induce activation of NF-κB likely act through various converging signal transduction pathways, including pathways involving activation of protein kinase C, Raf kinase and tyrosine kinases. The ability of antioxidants to inhibit NF-κB activation by various inducing agents suggests that reactive oxygen species are a converging point of such pathways (Siebenlist et al., supra, 1994).

Upon activation by an appropriate inducing agent, a Rel/NF-κB dimer is translocated into the nucleus, where it can activate gene transcription. The subcellular localization of a Rel/NF-κB is controlled by specific inhibitory proteins ("inhibitors of Rel/NF-κB" or "IκB's"), which noncovalently bind the Rel/NF-κB and mask its nuclear localization signal (NLS), thereby preventing nuclear uptake. Various IκB's, including, for example, IκBα, IκBβ, Bcl-3 and the Drosophila cactus gene product, have been identified (Bauerle and Baltimore, supra, 1996). In addition, Rel precursor proteins, such as p105 and p100, which are precursors of p50 and p52, respectively, function as IκB's (Siebenlist et al., supra, 1994). IκBα and IκBβ are expressed in most cell types and generally bind p65- and c-Rel-containing Rel/NF-κB dimers. Other IκB's appear to be expressed in a tissue specific manner (Thompson et al., *Cell* 80:573–582 (1995)).

IκB proteins are characterized by the presence of 5 to 8 ankyrin repeat domains, each about 30 amino acids, and a C-terminal PEST domain. For example, IκBα contains a 70 amino acid N-terminal domain, a 205 amino acid internal domain containing the ankyrin repeats, and a 42 amino acid C-terminal domain containing the PEST domain (Baldwin, supra, 1996). Although IκB proteins interact through their ankyrin repeats with the Rel homology domain of Rel/NF-κB dimers, binding of particular IκB proteins with particular Rel/NF-κB proteins appears to be relatively specific. For example, IκBα and IκBβ associate primarily with RelA- and c-Rel-containing Rel/NF-κB dimers, thereby blocking their nuclear localization signal. The binding of an IκB to NF-κB also interferes with the ability of NF-κB to bind DNA. However, whereas IκBα is phosphorylated following exposure of cells to tumor necrosis factor (TNF), IL-1, bacterial lipopolysaccharide (LPS) or phorbol esters, IκBβ is phosphorylated in certain cell types only in response to LPS or IL-1 (Baldwin, supra, 1996). However, in other cell types, IκBβ is phosphorylated in response to the same signals that induce IκBα, although with slower kinetics than IκBα (DiDonato et al., *Mol. Cell. Biol.* 16:1295–1304 (1996), which is incorporated herein by reference).

Formation of a complex between an IκB protein and a Rel protein is due to an interaction of the ankyrin domains with a Rel homology domain (Baeuerle and Baltimore, supra, 1996). Upon exposure to an appropriate stimulus, the IκB portion of the complex is rapidly degraded and the Rel/NF-κB portion becomes free to translocate to the cell nucleus. Thus, activation of a Rel/NF-κB does not require de novo protein synthesis and, therefore, occurs extremely rapidly. Consequently, activation of gene expression due to a Rel/NF-κB can be exceptionally rapid and provides an effective means to respond to an external stimulus. Such a rapid response of Rel/NF-κB transcription factors is particularly important since these factors are involved in the regulation of genes involved in the immune, inflammatory and acute phase responses, including responses to viral and bacterial infections and to various stresses.

Upon exposure of a cell to an appropriate inducing agent, IκBα, for example, is phosphorylated at serine residue 32 (Ser-32) and Ser-36 (Haskill et al., *Cell* 65:1281–1289 (1991)). Phosphorylation of IκBα triggers its rapid ubiquitination, which results in proteasome-mediated degradation of the inhibitor and translocation of active NF-κB to the nucleus (Brown et al., *Science* 267:1485–1488 (1995); Scherer et al., *Proc. Natl. Acad. Sci., USA*. 92:11259–11263 (1995); DiDonato et al., supra, 1996; DiDonato et al., *Mol. Cell. Biol.* 15:1302–1311 (1995); Baldi et al., *J. Biol. Chem.* 271:376–379 (1996)). The same mechanism also accounts for IκBβ degradation (DiDonato et al., supra, 1996).

Rel/NF-κB activation can be transient or persistent, depending on the inducing agent and the IκB that is phosphorylated. For example, exposure of a cell to particular cytokines induces IκBα phosphorylation and degradation, resulting in NF-κB activation, which induces the expression of various genes, including the gene encoding IκBα. The newly expressed IκBα then binds to NF-κB in the nucleus, resulting in its export to the cytoplasm and inactivation and, therefore, a transient NF-κB mediated response. In comparison, bacterial LPS induces IκBβ phosphorylation, resulting in NF-κB activation. However, the IκBβ gene is not induced by NF-κB and, as a result, activation of NF-κB is more persistent (Thompson et al., supra, 1995).

A constitutively active multisubunit kinase of approximately 700 kDa phosphorylates IκBα at Ser-32 and Ser-36 and, in some cases, requires polyubiquitination for activity (Chen et al., *Cell* 84:853–862 (1996); Lee et al., *Cell* 88:213–222 (1997)). The mitogen-activated protein kinase/ERK kinase kinase-1 (MEKK1) phosphorylates several proteins that copurify with this complex and have molecular weights of approximately 105 kDa, 64 kDa and 54 kDa; three other copurifying proteins having molecular weights of about 200 kDa, 180 kDa and 120 kDa are phosphorylated in the absence of MEKK1 (Lee et al., supra, 1997). However, a catalytically inactive MEKK1 mutant, which can block TNFα mediated activation of the jun kinase, does not block NF-κB activation (Lin et al., *Cell* 87:343–352 (1996)).

Overexpression of MEKK1 also induces the site-specific phosphorylation of IκBα in vivo and can directly activate IκBα in vitro by an ubiquitin-independent mechanism. However, MEKK1 did not phosphorylate IκBα at Ser-32 and Ser-36 in the in vitro experiments, indicating that it is not an IκBα kinase, but may act upstream of IκBα kinase in a signal transduction pathway (Lee et al., supra, 1997).

In addition to the above described ubiquitin dependent kinase 700 kDa complex, an ubiquitin independent 700 kDa complex, as well as an ubiquitin independent 300 kDa kinase complex phosphorylates IκBα Ser-32 and Ser-36, but not a mutant containing threonines substituted for these serines (Baeuerle and Baltimore, supra, 1996). The specific polypeptides responsible for the IκB kinase activity of these complexes have not been described.

A double stranded RNA-dependent protein kinase (PKR) that phosphorylates IκBα in vitro has been described (Kumar et al., *Proc. Natl. Acad. Sci., USA* 91:6288–6292 (1994)). Moreover, an antisense PKR DNA molecule prevented NF-κB activation by double stranded RNA, but did not prevent NF-κB activation by TNFα (Maran et al., *Science* 265:789–792 (1995)). Casein kinase II (CKII) also can interact with and phosphorylate IκBα, although weakly as compared to CKII phosphorylation of casein, and the Ser-32 and Ser-36 residues in IκBα represent CKII phosphorylation sites (Roulston et al., supra, 1995). However, all of the inducers of NF-κB activity do not stimulate these protein kinases to phosphorylate IκB, indicating that, if they are involved in NF-κB activation, these kinases, like MEKK1, operate upstream of the IκB kinase. Thus, a rapidly stimulated IκB kinase that directly phosphorylates IκBα on Ser-32 and Ser-36 and results in activation of NF-κB has not been identified.

A putative serine-threonine protein kinase has been identified in mouse cells by probing for nucleic acid molecules that encode proteins containing a consensus helix-loop-helix domain, which is involved in protein-protein interactions (Connelly and Marcu, supra, 1995). This putative kinase, which is ubiquitously expressed in various established cell lines, but differentially expressed in normal mouse tissues, was named CHUK (conserved helix-loop-helix ubiquitous kinase; GenBank Accession #U12473). In addition, a nucleic acid molecule (GenBank Accession #U22512) encoding a portion of a human CHUK protein that is 93% identical at the nucleotide level (95% identical at the amino acid level) with the mouse CHUK also was identified. However, neither the function of a CHUK protein in a cell nor a potential substrate for the putative kinase was described.

The present invention provides a substantially purified full length human IκB kinase, which phosphorylates IκBα on Ser-32 and Ser-36 and IκBβ on Ser-19 and Ser-23 (DiDonato et al., supra, 1996). As used herein, the term "substantially purified," when used in reference to an IαB kinase of the invention, means that the IκB kinase is relatively free from contaminating lipids, proteins, nucleic acids or other cellular material normally associated with IκB kinase a cell. A substantially purified human IκB kinase of the invention is a full length IκB kinase polypeptide, which can be expressed, for example, from a recombinant nucleic acid molecule such as SEQ ID NO: 1, or an IκB kinase protein, which can be substantially purified from a cell, for example, by a method of the invention comprising affinity chromatography using ATP and IκB as ligands (Example I).

The amino acid sequences for MEKK1 (GenBank Accession #U48596; locus RNU48596), PKR (GenBank Accession #M35663; locus HUMP68A) and CKII (GenBank Accession #M55268 J02924; locus HUMA1CKII) are different from the sequence of the IκB kinase disclosed herein (SEQ ID NO: 2) and, therefore, are distinguishable from the present invention. In addition, a full length human IκB kinase of the invention is distinguishable from the partial human CHUK polypeptide sequence in that the partial human CHUK polypeptide (Connelly and Marcu, supra, 1995; GenBank Accession #22512) lacks amino acids 1 to 31 as shown in SEQ ID NO: 2. As disclosed herein, a polypeptide having the amino acid sequence of the partial human CHUK polypeptide does not have IκB kinase activity when expressed in a cell, indicating that some or all of amino acid residues 1 to 31 are essential for kinase activity.

A full length human IκB kinase of the invention is exemplified by a protein kinase that has an apparent molecular mass of about 84 kDa and that phosphorylates IκBα on Ser-32 and Ser-36 (see Example I). As used herein, the term "full length," when used in reference to an IκB kinase of the invention, means a polypeptide having an amino acid sequence of an IκB kinase expressed normally in a cell. Such a normally expressed IκB kinase polypeptide begins with a methionine residue at its N-terminus (Met-1; see FIG. 1, SEQ ID NO: 2), the Met-1 being encoded by the initiator ATG (AUG) codon, and ends as a result of the termination of translation due to the presence of a STOP codon (see SEQ ID NO: 1). A full length human IκB kinase can be a native IκB kinase, which is substantially purified from a cell (see Example I), or can produced using recombinant DNA methods such as by expressing the nucleic acid molecule shown as SEQ ID NO: 1.

The apparent molecular mass of an IκB kinase can be measured using routine methods such as polyacrylamide gel electrophoresis performed in the presence of sodium dodecyl sulfate (SDS-PAGE) or column chromatography performed under reducing and denaturing conditions. In addition, the ability of an IκB kinase to phosphorylate IκBα on Ser-32 and Ser-36 can be identified using the methods disclosed herein.

With regard to the disclosed 84 kDa apparent molecular mass of a human IκB kinase of the invention, it is recognized that the apparent molecular mass of a previously unknown protein as determined, for example, by SDS-PAGE is an estimate based on the relative migration of the unknown protein as compared to the migration of several other proteins having known molecular masses. Thus, one investigator reasonably can estimate, for example, that an unknown protein has an apparent molecular mass of 82 kDa, whereas a second investigator, looking at the same unknown protein under substantially similar conditions, reasonably can estimate that the protein has an apparent molecular mass of 87 kDa. It is noted, for example, that the putative mouse CHUK protein is reported to have an apparent molecular mass of 85 kDa (Connelly and Marcu, supra, 1995), yet contains the same number of amino acid residues as the full length human IκB kinase (SEQ ID NO: 2). Accordingly, reference herein to an IκB kinase having an apparent molecular mass of "about 84 kDa" indicates that the kinase migrates by SDS-PAGE in an 8% gel under reducing conditions in the range of 80 kDa to 90 kDa, preferably in the range of 82 kDa to 87 kDa.

An IκB kinase of the invention is further exemplified by a substantially purified full length polypeptide comprising the amino acid sequence shown as SEQ ID NO: 2. In addition, the invention provides peptide portions of an IκB kinase, comprising at least two contiguous amino acids of SEQ ID NO: 2, including amino acid residue 30, preferably comprising at least four contiguous amino acids, including amino acid residue 30, and more preferably at least six contiguous amino acids, including amino acid residue 30. Thus, as used herein, the term "peptide portion," when used in reference to an IκB kinase of the invention, means at least three contiguous amino acids of SEQ ID NO: 2, including amino acid residue 30.

A peptide portion of an IκB kinase of the invention can be a tripeptide or larger, preferably a hexapeptide or larger, and more preferably a decapeptide or larger, up to a contiguous amino acid sequence having a maximum length that lacks one or more N-terminal or C-terminal amino acids of the full length polypeptide (SEQ ID NO: 2). Thus, a peptide portion of the IκB kinase having the amino acid sequence shown as SEQ ID NO: 2 can be from three amino acids long to 744 amino acids long, which is one residue less than the full length polypeptide, provided the peptide portion contains, in its proper position in the peptide relative to the full length polypeptide, amino acid 30 as shown in SEQ ID NO: 2.

A peptide portion of an IκB kinase of the invention can be produced by any of several methods well known in the art. For example, a peptide portion of an IκB kinase can be produced by enzymatic cleavage of an IκB kinase protein, which has been substantially purified as disclosed in Example I, using a proteolytic enzyme such as trypsin, chymotrypsin, Lys-C or the like, or combinations of such enzymes. Such proteolytic cleavage products can be purified using methods as disclosed in Example I, to obtain a peptide portion of an IκB kinase. A peptide portion of an IκB kinase also can be produced using methods of solution or solid phase peptide synthesis or can be expressed from a nucleic acid molecule such as a portion of the coding region of the nucleic acid sequence shown as SEQ ID NO: 1 or can be purchased from a commercial source.

A peptide portion of an IκB kinase can comprise the kinase domain of the IκB kinase and, therefore, can have the ability to phosphorylate an IκB protein. For example, a peptide portion of SEQ ID NO: 2 comprising amino acids 15 to 301 has the characteristics of a serine-threonine protein kinase domain (Hanks and Quinn, *Meth. Enzymol.* 200:38–62 (1991), which is incorporated herein by reference). Such a peptide portion of an IκB kinase can be examined for kinase activity by determining that it can phosphorylate IκBα at Ser-32 and Ser-36 or IκBβ at Ser-19 and Ser-23, using methods as disclosed herein. In addition, a peptide portion of an IκB kinase can comprise an immunogenic amino acid sequence of the IκB kinase and, therefore, can be useful for eliciting production of an antibody that can specifically bind the IκB kinase, particularly to an epitope comprising amino acid residue 30 as shown in SEQ ID NO: 2. Accordingly, the invention also provides anti-IκB kinase antibodies, which specifically bind to an IκB kinase, and IκB kinase-binding fragments of such antibodies. In addition, the invention provides cell lines producing anti-IκB kinase antibodies or IκB kinase-binding fragments thereof.

As used herein, the term "antibody" is used in its broadest sense to include polyclonal and monoclonal antibodies, as well as antigen binding fragments of such antibodies. With regard to an anti-IκB kinase antibody of the invention, the term "antigen" means an IκB kinase protein, polypeptide or peptide portion thereof. An anti-IκB kinase antibody, or antigen binding fragment of such an antibody, is characterized by having specific binding activity for an IκB kinase or a peptide portion thereof of at least about $1 \times 10^5$ M$^{-1}$. Thus, Fab, F(ab')$_2$, Fd and Fv fragments of an anti-IκB kinase antibody, which retain specific binding activity for an IκB kinase, are included within the definition of an antibody. In particular, an anti-IκB kinase antibody can react with the N-terminus of an IκB kinase, but not to a polypeptide having an amino acid sequence shown as residues 32 to 745 of SEQ ID NO: 2.

In addition, the term "antibody" as used herein includes naturally occurring antibodies as well as non-naturally occurring antibodies, including, for example, single chain antibodies, chimeric, bifunctional and humanized antibodies, as well as antigen-binding fragments thereof. Such non-naturally occurring antibodies can be constructed using solid phase peptide synthesis, can be produced recombinantly or can be obtained, for example, by screening combinatorial libraries consisting of variable heavy chains and variable light chains as described by Huse et al., *Science* 246:1275–1281 (1989), which is incorporated herein by reference. These and other methods of making, for example, chimeric, humanized, CDR-grafted, single chain, and bifunctional antibodies are well known to those skilled in the art (Winter and Harris, *Immunol. Today* 14:243–246 (1993); Ward et al., *Nature* 341:544–546 (1989) ; Harlow and Lane, *Antibodies: A laboratory manual* (Cold Spring Harbor Laboratory Press, 1988); Hilyard et al., *Protein Engineering: A practical approach* (IRL Press 1992); Borrabeck, *Antibody Engineering*, 2d ed. (Oxford University Press 1995); each of which is incorporated herein by reference).

Anti-IκB kinase antibodies can be raised using as an immunogen a substantially purified full length human IκB kinase, which can be prepared from natural sources or produced recombinantly, or a peptide portion of a human IκB kinase as defined herein, including synthetic peptides as described above. A non-immunogenic peptide portion of an IκB kinase can be made immunogenic by coupling the hapten to a carrier molecule such bovine serum albumin (BSA) or keyhole limpet hemocyanin (KLH), or by expressing the peptide portion as a fusion protein. Various other carrier molecules and methods for coupling a hapten to a carrier molecule are well known in the art and described, for example, by Harlow and Lane, supra, 1988). It is recognized that, due to the apparently highly amino acid sequence identity of the full length human IκB kinase and mouse CHUK, the amino acid sequences of IκB kinases may be highly conserved among species, particularly among mammalian species. However, antibodies to highly conserved proteins have been raised successfully in chickens. Such a method can be used to obtain an antibody to an IκB kinase, if desired.

Particularly useful antibodies of the invention are those that bind to an activated IκB kinase but not to an inactive IκB kinase, and, conversely, those that bind to an inactive form of the kinase but not to the activated form. For example, an IκB kinase can be activated by phosphorylation and, therefore, an antibody that recognizes the phosphorylated form of the IκB kinase, but that does not bind to the unphosphorylated form can be obtained. In addition, IκB kinase can be activated by release of a regulatory subunit and, therefore, an antibody that recognizes the form of IκB kinase that is not bound to the regulatory subunit can be obtained. Such antibodies are useful for identifying the presence of active IκB kinase in a cell.

An anti-IκB kinase antibody is useful, for example, for determining the presence or level of an IκB kinase in a tissue sample, which can be a lysate or a histological section. The identification of the presence or level of an IκB kinase in the sample can be made using well known immunoassay and immunohistochemical methods (Harlow and Lane, supra, 1988). An anti-IκB kinase antibody also can be used to substantially purify an IκB kinase from a sample and, in addition, can copurify a protein such as an IκB kinase regulatory protein subunit that is bound to the IκB kinase. Such a regulatory protein, which can copurify with an IκB kinase can be, for example, an 86 kDa protein as disclosed herein (see Example I). In addition, an anti-IκB kinase antibody can be used in a screening assay to identify agents that alter the activity of the IκB kinase.

A kit incorporating an anti-IκB kinase antibody, which can be specific for the active or inactive form of IκB kinase or can bind to the IκB kinase regardless of the activity state, can be particularly useful. Such a kit can contain, in addition to an anti-IκB kinase antibody, a reaction cocktail that provides the proper conditions for performing the assay, control samples that contain known amounts of an IκB kinase and, if desired, a second antibody specific for the anti-IκB kinase antibody. Such an assay also should include a simple method for detecting the presence or amount of an IκB kinase in a sample that is bound to the anti-IκB kinase antibody.

A protein such as anti-IκB kinase antibody, as well as an IκB kinase or peptide portion thereof, can be labeled so as to be detectable using methods well known in the art (Hermanson, "Bioconjugate Techniques" (Academic Press 1996), which is incorporated herein by reference; Harlow and Lane, 1988; chap. 9). For example, a protein can be labeled with various detectable moieties including a radiolabel, an enzyme, biotin or a fluorochrome. Reagents for labeling a protein such as an anti-IκB kinase antibody can be included in a kit containing the protein or can be purchased separately from a commercial source.

Following contact, for example, of a labeled antibody with a sample such as a tissue homogenate or a histological section of a tissue, specifically bound labeled antibody can be identified by detecting the particular moiety. Alternatively, a labeled second antibody can be used to identify specific binding of an unlabeled anti-IκB kinase antibody. A second antibody generally will be specific for the particular class of the first antibody. For example, if an anti-IκB kinase antibody is of the IgG class, a second antibody will be an anti-IgG antibody. Such second antibodies are readily available from commercial sources. The second antibody can be labeled using a detectable moiety as described above. When a sample is labeled using a second antibody, the sample is first contacted with a first antibody, which is an anti-IκB kinase antibody, then the sample is contacted with the labeled second antibody, which specifically binds to the anti-IκB kinase antibody and results in a labeled sample.

Methods for raising polyclonal antibodies, for example, in a rabbit, goat, mouse or other mammal, are well known in the art. In addition, monoclonal antibodies can be obtained using methods that are well known and routine in the art (Harlow and Lane, supra, 1988). Essentially, spleen cells from an IκB kinase-immunized mouse can be fused to an appropriate myeloma cell line such as SP/02 myeloma cells to produce hybridoma cells. Cloned hybridoma cell lines can be screened using labeled IκB kinase protein to identify clones that secrete anti-IκB kinase monoclonal antibodies. Hybridomas expressing anti-IκB kinase monoclonal antibodies having a desirable specificity and affinity can be isolated and utilized as a continuous source of the antibodies, which are useful, for example, for preparing standardized kits as described above. Similarly, a recombinant phage that expresses, for example, a single chain anti-IκB kinase also provides a monoclonal antibody that can used for preparing standardized kits.

A monoclonal anti-IκB kinase antibody can be used to prepare anti-idiotypic antibodies, which presents an epitope that mimics the epitope recognized by the monoclonal antibody used to prepare the anti-idiotypic antibodies. Where the epitope to which the monoclonal antibody includes, for example, a portion of the IκB kinase domain, the anti-idiotypic antibody can act as a competitor of IκBand, therefore, can be useful for reducing the level of phosphorylation of IκB and, consequently, the activity of NF-κB.

The present invention further provides methods of identifying an agent that can alter the association of an IκB kinase with a second protein, which can be an upstream activator, a downstream effector such as IκB, or an interacting regulatory protein of the IκB kinase. As used herein, the term "associate" or "association," when used in reference to an IκB kinase and a second protein means that the kinase and the second protein have a binding affinity for each other such that they form a bound complex in vivo or in vitro, including in a cell in culture or in a reaction comprising substantially purified reagents. For convenience, the term "bind" or "interact" is used interchangeably with the term "associate."

The affinity of binding of an IκB kinase and a second protein such as an IκB is characterized in that it is sufficiently specific such that a bound complex can form in vivo in a cell or can form in vitro under appropriate conditions as disclosed herein. The formation or dissociation of a bound complex can be identified, for example, using the two hybrid assay or demonstrating coimmunoprecipitation of the second protein with the IκB kinase, as disclosed herein, or using other well known methods such as equilibrium dialysis. Methods for distinguishing the specific association of an IκB kinase and a second protein from nonspecific binding to the IκB kinase are known in the art and, generally, include performing the appropriate control experiments to demonstrate the absence of nonspecific protein binding.

As used herein, the term "second protein" refers to a protein that specifically associates with an IκB kinase. Such a second protein is exemplified herein by IκB proteins, including IκBα and IκBβ, which are substrates for IκB kinase activity and are downstream of the IκB kinase in a signal transduction pathway that results in the regulated expression of a gene. Agents that alter the association of an IκB kinase and an IκB protein can be extremely valuable, for example, for limiting excessive cytokine expression as occurs in an acute phase response by preventing the activation of NF-κB, thereby preventing NF-κB mediated induction of cytokine gene expression. Where, in a drug screening assay of the invention, the second protein is an IκB, the IκB kinase can be any protein having IκB kinase activity, including, for example, mouse CHUK (Connelly and Marcu, supra, 1995; GenBank Accession #12473), which, prior to the present disclosure, was not known to have the ability to associate with IκB or to phosphorylate IκB.

In addition, a second protein can be a protein that is upstream of IκB kinase in a signal transduction pathway and associates with the IκB kinase. Such a second protein, which can be an upstream activator of the IκB kinase, can be identified using routine methods for identifying protein-protein interactions as disclosed herein. Such second proteins can be, for example, MEKK1 or PKR or CKII, each of which has been reported be involved in a pathway leading to phosphorylation of IκB and activation of NF-κB but neither of which has the characteristics expected of the common IκB kinase present at the point where the various NF-κB activation pathways converge (see, for example, Lee et al., supra, 1997).

A second protein also can be a regulatory protein, which associates with an IκB kinase. Such a regulatory protein can inhibit or activate IκB kinase activity depending, for example, on whether the regulatory protein is associated with IκB kinase. The regulatory protein also can be important for "docking" the catalytic IκB kinase subunit to its substrate. The ability of a regulatory protein to associate with, or dissociate from, IκB kinase can depend, for example, on the relative phosphorylation state of the regulatory protein. It is recognized that an upstream activator of IκB kinase also can interact with such a regulatory protein, thereby indirectly inhibiting or activating the IκB kinase.

As disclosed herein, two copurifying proteins were isolated by ATP and IκB affinity chromatography and identified by SDS-PAGE (Example I). Partial amino acid sequences were determined and cDNA molecules encoding one of the proteins and a portion of second were obtained. One of the proteins has an apparent molecular mass of 84 kDa. Expression in a cell of a cDNA molecule encoding the 84 kDa protein results in increased NF-κB activity following cytokine induction as compared to control cells, whereas expression of the antisense of this cDNA decreases the basal NF-κB activity in the cells and prevents cytokine induction of NF-κB activity. Based on these functional analyses, the 84 kDa protein was determined to be an IκB kinase. The second protein, which copurified with the 84 kDa IκB kinase, has an apparent molecular mass of 86 kDa. While not wishing to be bound to any potential mechanism by which IκB kinase activity is regulated, it is noted that the 86 kDa protein that copurifies with the 84 kDa IκB kinase has characteristics expected of an IκB kinase regulatory protein. For example, incubation of a cell extract containing active IκB kinase with a phosphatase inactivates the IκB kinase activity, and the presence of okadaic acid, which is a phosphatase inhibitor, blocks the inactivation of the IκB kinase by the phosphatase. Furthermore, such inactivated IκB kinase can be reactivated by incubation with a cell extract prepared from TNFα stimulated cells. However, phosphorylation of the 84 kDa IκB kinase is not associated with this reactivation but, instead, the 86 kDa protein that copurifies with the 84 kDa IκB kinase is phosphorylated. These results reasonably can be interpreted to indicate that the 84 kDa IκB kinase is a catalytic subunit of a larger complex, which also comprises the 86 kDa protein, which can be a regulatory subunit.

The ability of the 84 kDa IκB kinase to associate with a second protein such as a regulatory subunit as well as with IκB is suggested, for example, by the presence in the IκB kinase of two different protein binding domains, a helix-loop-helix domain and a leucine zipper (see Connelly and Marcu, supra, 1995). In addition, kinases such as MEKK1, PRK and CKII, the activities of which are associated with phosphorylation of IκBα, reportedly are upstream of a putative IκB kinase, suggesting that these kinases may act by phosphorylating IκB kinase. As disclosed herein, however, the 84 kDa IκB kinase is not phosphorylated following reactivation of phosphatase-treated cell extracts containing the kinase; instead, the 86 kDa protein that copurifies with the 84 kDa IκB kinase is phosphorylated. Thus, if phosphorylation is the mechanism by which a signal is transmitted to and activates the IκB kinase, a regulatory protein that associates with the IκB kinase, such as the copurifying 86 kDa protein, may be the target for phosphorylation by an upstream activating protein kinase such as MEKK1.

A screening assay of the invention provides a means to identify an agent that alters the association of an IκB kinase with a second protein. As used herein, the term "modulate" or "alter" when used in reference to the association of an IκB kinase and a second protein, means that the affinity of the association is increased or decreased. Agents that can alter the association of an IκB kinase with a second protein can be useful for modulating the level of phosphorylation of IκB in a cell, which, in turn, modulates the activity of NF-κB in the cell and the expression of a gene regulated by NF-κB. Such an agent can be, for example, an anti-idiotypic antibody as described above, which can inhibit the association of an IκB kinase and IκB, is example of such an agent. A peptide portion of IκBα comprising amino acids 32 to 36, but containing substitutions for Ser-32 and Ser-36, is another example of such an agent, since the peptide can compete with IκBα binding to an IκB kinase, as is the corresponding peptide of IκBβ.

A screening assay of the invention also is useful for identifying agents that directly alter the activity of an IκB kinase. While such an agent can act, for example, by altering the association of the IκB kinase with a second protein, the agent also can act directly as a specific activator or inhibitor of the kinase activity. Specific protein kinase inhibitors include, for example, staurosporin, the heat stable inhibitor of cAMP-dependent protein kinase, and the MLCK inhibitor, which are known in the art and commercially available.

As disclosed herein, activity of an IκB kinase can be measured by identifying phosphorylation, for example, of IκBα, either directly or using an antibody specific for the Ser-32 and Ser-36 phosphorylated form of IκBα. An antibody that binds to IκBα that is phosphorylated on Ser-32, for example, can be purchased from a commercial source (New England Biolabs; Beverly Mass.). Cultured cells can be exposed to various agents suspected of having the ability to directly alter IκB kinase activity, then aliquots of the cells either are collected or are treated with a proinflammatory stimulus such as a cytokine, then collected. The collected cells are lysed and the kinase is immunoprecipitated using an anti-IκB kinase antibody. A substrate such as IκBα or IκBβ is added to the immunocomplex and the ability of the kinase to phosphorylate the substrate is determined as described above. If desired, the anti-IκB kinase antibody first can be coated onto a plastic surface such as in 96 well plates, then the cell lysate is added to the wells under conditions that allow binding of IκB kinase by the antibody. Following washing of the wells, IκB kinase activity is measured as described above. Such a method is extremely rapid and provides the additional advantage that it can be automated for high through-put assays.

A screening assay of the invention is particularly useful to identify, from among a diverse population of molecules, those agents that modulate the association of an IκB kinase and a second protein or that directly alter the activity of the IκB kinase. Methods for producing libraries containing diverse populations of molecules, including chemical or biological molecules such as simple or complex organic molecules, peptides, proteins, peptidomimetics, glycoproteins, lipoproteins, polynucleotides, and the like, are well known in the art (Huse, U.S. Pat. No. 5,264,563, issued Nov. 23, 1993; Blondelle et al., *Trends Anal. Chem.* 14:83–92 (1995); York et al., *Science* 274:1520–1522 (1996); Gold et al., *Proc. Natl. Acad. Sci., USA* 94:59–64 (1997); Gold, U.S. Pat. No. 5,270,163, issued Dec. 14, 1993). Such libraries also can be obtained from commercial sources.

Since libraries of diverse molecules can contain as many as $10^{14}$ to $10^{15}$ different molecules, a screening assay of the invention provides a simple means for identifying those agents in the library that can modulate the association of an IκB kinase and a second protein or can alter the activity of an IκB kinase. In particular, a screening assay of the invention can be automated, which allows for high throughput screening of randomly designed libraries of agents to identify those particular agents that can modulate the ability of an IκB kinase and a second protein to associate or alter the activity of the kinase.

A drug screening assay of the invention utilizes an IκB kinase, which can be expressed, for example, from a nucleic acid molecule encoding the amino acid sequence shown in SEQ ID NO: 2 or purified as disclosed herein, or can utilize an IκB kinase fusion protein such as an IκB kinase-glutathione-S-transferase (GST) or IκB kinase-histidine$_6$ (His-6) fusion protein (see Example III). The IκB kinase or IκB kinase fusion protein is characterized, in part, by having an affinity for a solid substrate as well as having the ability to specifically associate with an appropriate second protein such as an IκB protein. For example, when IκB kinase is used in a screening assay, the solid substrate can contain a covalently attached anti-IκB kinase antibody, provided that the antibody binds the IκB kinase without interfering with the ability of the IκB kinase to associate with the second protein. Where an IκB kinase-GST fusion protein is used in such a screening assay, the solid substrate can contain covalently attached glutathione, which is bound by the GST component of the fusion protein.

A drug screening assay to identify an agent that alters the association of an IκB kinase and a second protein can be performed by allowing, for example, the IκB kinase or IκB kinase-fusion protein to bind to the solid support, then adding the second protein, which can be an IκB such as IκBα, and an agent to be tested, under conditions suitable for the association of the IκB kinase and IκBα in the absence of a drug (see Example III). As appropriate, the IκB kinase can be activated or inactivated as disclosed herein and, typically, the IκB kinase or the second protein is detectably labeled so as to facilitate identification of the association. Control reactions, which contain or lack either, the IκB kinase (or fusion protein), or the IκB protein, or the agent, or which substitute the IκB protein with a second protein that is known not to associate specifically with the IκB kinase, also are performed. Following incubation of the reaction mixture, the amount of IκBα specifically bound to IκB kinase in the presence of an agent can be determined and compared to the amount of binding in the absence of the agent so that agents that modulate the association can be identified.

A protein such as an IκB kinase used in a screening assay can be detectably labeled with a radionuclide, a fluorescent label, an enzyme, a peptide epitope or other such moiety, which facilitates a determination of the amount of association in a reaction. By comparing the amount of specific binding of an IκB kinase and IκB in the presence of an agent as compared to the control level of binding, an agent that increases or decreases the binding of the IκB kinase and IκB can be identified. In comparison, where a drug screening assay is used to identify an agent that alters the activity of an IκB kinase, the detectable label can be, for example, $\gamma$-$^{32}$P-ATP, and the amount of $^{32}$P-IκB can be detected as a measure of IκB kinase activity. Thus, the drug screening assay provides a rapid and simple method for selecting agents that desirably alter the association of an IκB kinase and a second protein such as an IκB or for altering the activity of an IκB kinase. Such agents can be useful, for example, for modulating the activity of NF-κB in a cell and, therefore, can be useful as medicaments for the treatment of a pathology due, at least in part, to aberrant NF-κB activity.

The method for performing a drug screening assay as disclosed herein also provides a research tool for identifying a target of drug that is or can be used therapeutically to ameliorate an undesirable inflammatory or immune response, but for which the target of the drug is not known. Cytokine restraining agents, for example, are a class of agents that can alter the level of cytokine expression (U.S. Pat. No. 5,420,109, issued May 30, 1995) and can be used to treat various pathologies, including patho-immunogenic diseases such as rheumatoid arthritis and those induced by exposure to bacterial endotoxin such as occur in septic shock (see, also, WO96/27386, published Sep. 12, 1996).

The specific cellular target upon which a cytokine restraining agent acts has not been reported. However, the myriad of pathologic effects ameliorated by such agents are similar to various pathologies associated with aberrant NF-κB activity, suggesting that cytokine restraining agents may target an effector molecule in a NF-κB signal transduction pathway. Thus, one potential target of a cytokine restraining agent can be an IκB kinase. Accordingly, a screening assay of the invention can be used to determine whether a cytokine restraining agent alters the activity of IκB kinase or alters the association of IκB kinase and a second protein such as IκB. If it is determined that a cytokine restraining agent has such an effect, the screening assay then can be used to screen a library of cytokine regulatory agents to identify those having desirable characteristics, such as those having the highest affinity for the IκB kinase.

The invention also provides a method of obtaining substantially purified IκB kinase from a sample by 1) incubating the sample containing the kinase with ATP, which is immobilized on a matrix, under conditions suitable for binding of the kinase to the ATP; 2) obtaining from the immobilized ATP a fraction of the sample containing the kinase; 3) incubating the fraction containing the IκB kinase with an IκB, which is immobilized on a matrix, under conditions suitable for binding of the kinase to the IκB; and 4) obtaining from the immobilized IκB substantially purified IκB kinase. Such a method of purifying an IκB kinase is exemplified herein by the use of ATP affinity chromatography and IκBα affinity chromatography to substantially purify IκB kinase from a sample of HeLa cells (see Example I).

The skilled artisan will recognize that a ligand such as ATP or an IκB also can be immobilized on various other matrices, including, for example, on magnetic beads, which provide a rapid and simple method of obtaining a fraction containing an ATP- or an IκB-bound IκB kinase from the remainder of the sample. Methods for immobilizing a ligand such as ATP or an IκB are well known in the art (Haystead et al., *Eur. J. Biochem.* 214:459–467 (1993), which is incorporated herein by reference; see, also, Hermanson, supra, 1996). Similarly, the artisan will recognize that a sample containing IκB kinase can be a cell, tissue or organ sample, which is obtained from an animal, including a mammal such as a human, and prepared as a lysate; or can be a bacterial, insect, yeast or mammalian cell lysate, in which the IκB kinase is expressed from a recombinant nucleic acid molecule encoding the kinase.

The invention also provides a method of identifying a second protein that associates with an IκB kinase. A transcription activation assay such as the yeast two hybrid system is particularly useful for the identification of protein-protein interactions (Fields and Song, *Nature* 340:245–246 (1989), which is incorporated herein by reference). In addition, the two hybrid assay is useful for the manipulation of protein-protein interaction and, therefore, also is useful in a screening assay to identify agents that modulate the specific interaction.

A transcription activation assay such as the two hybrid assay also can be performed in mammalian cells (Fearon et al., *Proc. Natl. Acad. Sci., USA* 89:7958–7962 (1992), which is incorporated herein by reference). However, the yeast two hybrid system provides a particularly useful assay due to the ease of working with yeast and the speed with which the assay can be performed. Thus, the invention also provides methods of identifying proteins that can interact with an IκB kinase, including proteins that act as upstream activators or downstream effectors of the IκB kinase in a signal transduction pathway mediated by the IκB kinase or proteins that bind to and regulate the activity of the IκB kinase. Such proteins that interact with an IκB kinase can be involved, for example, in tissue specific regulation of NF-κB activation or constitutive NF-κB activation and consequent gene expression.

The conceptual basis for a transcription activation assay is predicated on the modular nature of transcription factors, which consist of functionally separable DNA-binding and trans-activation domains. When expressed as separate proteins, these two domains fail to mediate gene transcription. However, the ability to activate transcription can be restored if the DNA-binding domain and the trans-activation domain are bridged together through a protein-protein interaction. These domains can be bridged, for example, by expressing the DNA-binding domain and trans-activation domain as fusion proteins (hybrids), where the proteins that are appended to these domains can interact with each other. The protein-protein interaction of the hybrids can bring the DNA-binding and trans-activation domains together to create a transcriptionally competent complex.

One adaptation of the transcription activation assay, the yeast two hybrid system, uses S. cerevisiae as a host cell for vectors that express the hybrid proteins. For example, a yeast host cell containing a reporter lacZ gene linked to a LexA operator sequence can be used to identify specific interactions between an IκB kinase and a second protein, where the DNA-binding domain is the LexA binding domain, which binds the LexA promoter, and the trans-activation domain is the B42 acidic region. When the LexA domain is bridged to the B42 trans-activation domain through the interaction of an IκB kinase with a second protein, which can be expressed, for example, from a cDNA library, transcription of the reporter lacZ gene is activated. In this way, proteins that interact with the IκB kinase can be identified and their role in a signal transduction pathway mediated by the IκB kinase can be elucidated.

In addition to identifying proteins that were not previously known to interact with an IκB kinase, a transcription activation assay such as the yeast two hybrid system also is useful as a screening assay to identify agents that alter association of an IκB kinase and a second protein known to bind the IκB kinase. Thus, as described above for in vitro screening assays, a transcription activation assay can be used to screen a panel of agents to identify those agents particularly useful for altering the association of an IκB kinase and a second protein in a cell. Such agents can be identified by detecting an altered level of transcription of a reporter gene, as described above, as compared to the level of transcription in the absence of the agent. For example, an agent that increases the interaction between an IκB kinase and IκBα can be identified by an increased level of transcription of the reporter gene as compared to the control level of transcription in the absence of the agent. Such a method is particularly useful because it identifies an agent that alters the association of an IκB kinase and a second protein in a living cell.

In some cases, an agent may not be able to cross the yeast cell wall and, therefore, cannot enter the yeast cell to alter a protein-protein interaction. The use of yeast spheroplasts, which are yeast cells that lack a cell wall, can circumvent this problem (Smith and Corcoran, In *Current Protocols in Molecular Biology* (ed. Ausubel et al.; Green Publ., NY 1989), which is incorporated herein by reference). In addition, an agent, upon entering a cell, may require "activation" by a cellular mechanism that may not be present in yeast. Activation of an agent can include, for example, metabolic processing of the agent or a modification such as phosphorylation of the agent, which can be necessary to confer activity upon the agent. In this case, a mammalian cell line can be used to screen a panel of agents (Fearon et al., supra, 1992).

An agent that alters the catalytic activity of an IκB kinase or that alters the association of an IκB kinase and a second protein such as IκBα or an IκB kinase regulatory subunit or an upstream activator of an IκB kinase can be useful as a drug to reduce the severity of a pathology characterized by aberrant NF-κB activity. For example, a drug that increases the activity of an IκB kinase or that increase the affinity of an IκB kinase and IκBα can increase the amount of IκBα phosphorylated as Ser-32 or Ser-36 and, therefore, increase the amount of active NF-κB and the expression of a gene regulated by NF-κB, since the drug will increase the level of phosphorylated IκBα in the cell, thereby allowing NF-κB translocation to the nucleus. In contrast, a drug that decreases or inhibits the catalytic activity of an IκB kinase or the association of IκB kinase and IκBα can be useful where it is desirable to decrease the level of active NF-κB in a cell and the expression of a gene induced by activated NF-κB. It should be recognized that an antisense IκB kinase molecule of the invention also can be used to decrease IκB kinase activity in a cell by reducing or inhibiting its expression or by reducing or inhibiting its responsiveness to an inducing agent such as TNFα, Il-1 or phorbol ester (see Example II). Accordingly, the invention also provides methods of treating an individual suffering from a pathology characterized by aberrant NF-κB activity by administering to the individual an agent that modulates the catalytic activity of an IκB kinase or that alters the association of an IκB kinase and a second protein such as IκBα.

An agent that decreases the activity of an IκB kinase or otherwise decreases the amount of IκB phosphorylation in a cell can reduce or inhibit NF-κB mediated gene expression, including, for example, the expression of proinflammatory molecules such as cytokines and other biological effectors involved in an inflammatory, immune or acute phase response. The ability to reduce or inhibit such gene expression can be particularly valuable for treating various pathological conditions such as rheumatoid arthritis, asthma and septic shock, which are characterized or exacerbated by the expression of such proinflammatory molecules.

Glucocorticoids are potent anti-inflammatory and immunosuppressive agents that are used clinically to treat various pathologic conditions, including autoimmune diseases such as rheumatoid arthritis, systemic lupus erythematosis and asthma. Glucocorticoids suppress the immune and inflammatory responses, at least in part, by increasing the rate of IκBα synthesis, resulting in increased cellular levels of IκBα, which bind to and inactivate NF-κB (Scheinman et al., Science 270:283–286 (1995); Auphan et al., Science 270:286–290 (1995)). Thus, glucocorticoids suppress NF-κB mediated expression of genes encoding, for example, cytokines, thereby suppressing the immune, inflammatory and acute phase responses. However, glucocorticoids and glucocorticoid-like steroids also are produced physiologically and are required for normal growth and development. Unfortunately, prolonged treatment of an individual with higher than physiological amounts of glucocorticoids produces clinically undesirable side effects. Thus, the use of an agent that alters the activity of an IκB kinase or that alters the association of an IκB kinase and a second protein, as identified using a method of the invention, can provide a means for selectively altering NF-κB activity without producing some of the undesirable side effects associated with glucocorticoid treatment.

Inappropriate regulation of Rel/NF-κB transcription factors is associated with various human diseases. For example, many viruses, including human immunodeficiency virus-1 (HIV-1), herpes simplex virus-1 (HSV-1) and cytomegalovirus (CMV) contain genes regulated by a κB regulatory element and these viruses, upon infecting a cell, utilize cellular Rel/NF-κB transcription factors to mediate viral gene expression (Siebenlist et al., supra, 1994). Tat-mediated transcription from the HIV-1 enhancer, for example, is decreased if the NF-κB and SP1 binding sites are deleted from the enhancer/promotor region, indicating that Tat interacts with NF-κB, SP1 or other transcription factors bound at this site to stimulate transcription (Roulston et al., Microbiol. Rev. 59:481–505 (1995)). In addition, chronic HIV-1 infection, and progression to AIDS, is associated with the development of constitutive NF-κB DNA binding activity in myeloid cells (Roulston et al., supra, 1995). Thus, a positive autoregulatory loop is formed, whereby HIV-1 infection results in constitutively active NF-κB, which induces expression of HIV-1 genes (Baeuerle and Baltimore, Cell 87:13-20 (1996). Constitutive NF-κB activation also may protect cells against apoptosis, preventing clearance of virus-infected cells by the immune system (Liu et al., Cell 87:565–576 (1996)).

An agent that decreases the activity of an IκB kinase or that alters the association of an IκB kinase and a second protein such that IκB phosphorylation is decreased can be useful for reducing the severity of a viral infection such as HIV-1 infection in an individual by providing increased levels of unphosphorylated IκB in virus-infected cells. The unphosphorylated IκB then can bind to NF-κB in the cell, thereby preventing nuclear translocation of the NF-κB and viral gene expression. In this way, the rate of expansion of the virus population can be limited, thereby providing a therapeutic advantage to the individual.

In addition, the decreased level of NF-κB activity may allow the virus-infected cell to undergo apoptosis, resulting in a decrease in the viral load in the individual. As such, it can be particularly useful to treat virus-infected cells ex vivo with an agent identified using a method of the invention. For example, peripheral blood mononuclear cells (PMBCs) can be collected from an HIV-1 infected individual and treated in culture with an agent that decreases the activity of an IκB kinase or alters the association of the IκB kinase with an IκB. Such a treatment can be useful to purge the PMBCs of the virus-infected cells by allowing apoptosis to proceed. The purged population of PBMCs then can be expanded, if desired, and readministered to the individual.

Rel/NF-κB proteins also are involved in a number of different types of cancer. For example, the adhesion of cancer cells to endothelial cells is increased due to treatment of the cancer cells with IL-1, suggesting that NF-κB induced the expression of cell adhesion molecules, which mediated adherence of the tumor cells to the endothelial cells; agents such as aspirin, which decrease NF-κB activity, blocked the adhesion by inhibiting expression of the cell adhesion molecules (Tozawa et al., Cancer Res. 55:4162–4167 (1995)). These results indicate that an agent that decreases the activity of an IκB kinase or that decrease the association of an IκB kinase and IκB can be useful for reducing the likelihood of metastasis of a tumor in an individual.

As discussed above for virus-infected cells, constitutive NF-κB activation also may protect tumor cells against programmed cell death as well as apoptosis induced by chemotherapeutic agents (Liu et al., Cell 87:565–576 (1996); Baeuerle and Baltimore, Cell 87:13–20 (1996)). Thus, an agent that decreases IκB kinase activity or that decreases the association of IκB kinase and IκB also can be useful for allowing programmed cell death to occur in a tumor cell by increasing the level of unphosphorylated IκB, which can bind NF-κB and decrease the level of active NF-κB in the tumor cell.

The following examples are intended to illustrate but not limit the present invention.

EXAMPLE I

Identification and Characterization of a Human IκB Kinase

This example provides a method for identifying and isolating a cytokine responsive protein kinase that phosphorylates IκB, which regulates NF-κB activity.

A. Kinase Assays:

Kinase assays were performed using GST fusion proteins containing amino acid residues 1 to 54 of IκB. The fusion proteins were linked to glutathione SEPHAROSE and the beads were used directly in the assays. At earlier stages in the purification of the IκB kinase, the beads were washed prior to loading onto the gel to minimize contributions from other proteins. In some of the later characterization of highly purified material, soluble fusion protein was used.

Three distinct substrates for the IκB kinase were used: 1) substrate "WT" contained amino acid residues 1 to 54 of IκBα; 2) substrate "AA" contained amino acid residues 1 to 54 of IκBα, except that S32 and S36 were replaced with A32 and A36, respectively; and 3) substrate "TT" contained amino acid residues 1 to 54 of IκBα, except that S32 and S36 were replaced with T32 and T36, respectively (DiDonato et al., *Mol. Cell. Biol.* 16:1295–1304 (1996)). Each substrate was expressed as a GST fusion protein. The physiologic, inducible IκB kinase is specific for S32 and S36 (WT) in IκBα, but does not recognize the TT or AA mutants (DiDonato et al., *Mol. Cell. Biol.* 16:1295–1304 (1996)).

Kinase assays were carried out in 20 mM HEPES (pH 7.5–7.6), 20 mM β-glycerophosphate (β-GP), 10 mM $MgCl_2$, 10 mM PNPP, 100 μM $Na_3VO_4$, 2 mM dithiothreitol (DTT), 20 μM ATP, 10 μg/ml aprotinin. NaCl concentration was 150–200 mM and the assays were carried out at 30° C. for 30 min. Fractionation was performed by SDS-PAGE, followed by quantitation by phosphoimager analysis.

B. Purification of IκB Kinase:

The protein purification buffer (Buffer A) consisted of 20 mM Tris (pH 7.6, measured at RT), 20 mM NaF, 20 mM β-GP, 1 mM PNPP, 500 μM $Na_3VO_4$, 2 mM DTT, 2.5 mM metabisulfite, 5 mM benzamidine, 1 mM EDTA, 0.5 mM EGTA, 1 mM PMSF, and 10% glycerol. Brij-35 was added as indicated. Cell lysis buffer was Buffer A containing an additional 19 mM PNPP, 20 mM β-GP and 500 μM $Na_3VO_4$, and 20 μg/ml aprotinin, 2.5 μg/ml leupeptin, 8.3 μg/ml bestatin, 1.7 μg/ml pepstatin.

Purification was performed using 5 to 130 liters of HeLa S3 cells. For illustration, the procedure for a 15 liter preparation is presented. All purification steps were performed in a cold room at 4° C.

In order to activate the IκB kinase, cells were stimulated with TNFα prior to purification. TNFα was either recombinant TNFα, which was purchased from R&D Systems and used at 20 ng/ml, or His-tagged TNFα, which was expressed and partially purified from *E. coli* and used at 5 μg/ml. TNFα-induced HeLa S3 cell killing activity assays were performed in the presence of cycloheximide and indicated that the partially purified His-tagged TNFα had approximately one-tenth the activity of the commercial TNFα.

Fifteen liters of HeLa S3 cells were grown in suspension in high glucose Dulbecco's modified Eagle's medium supplemented wirh 10% calf serum, 2 mg/ml L-glutamine, 100 U/ml penicillin/streptomycin, 0.11 mg/ml sodium pyruvate, and 1×nonessential amino acids (Irvine Scientific; Irvine Calif.). Cell density was approximately $5 \times 10^5$ cells/ml at the time of collection. Cells were concentrated tenfold by centrifugation, stimulated for 5 min with TNFα at 37° C., then diluted with 2.5 volumes of ice cold phosphate buffered saline (PBS) containing 50 mM NaF and pelletted at 2000× g. The cell pellet was washed once with ice cold PBS/50 mM NaF, then suspended in lysis buffer, quick frozen in liquid nitrogen and stored at −80° C.

For purification of IκB kinase, cells were thawed and cytoplasmic extract prepared. Lysis was achieved by 40 strokes in an all glass Dounce homogenizer (pestle A) in lysis buffer containing 0.05% NP-40 on ice. The homogenate was centrifuged at 12,000 rpm for 19 min in a Beckman SS34 rotor at 4° C.

Supernatant was collected and centrifuged at 38,000 rpm for 80 min in a Beckman 50.1 Ti rotor at 4° C. The supernatant (S100 fraction) was quick frozen in liquid nitrogen and stored at −80° C. Small aliquots of S100 material, prepared from either unstimulated HeLa cells or from TNFα stimulated cells, were purified in a single passage over a SUPEROSE 6 gel filtration column (1.0×30 cm; Pharmacia; Uppsalla Sweden) equilibrated in Buffer A containing 0.1% Brij-35 and 300 mM NaCl and eluted at a flowrate of 0.3 ml/min. 0.6 ml fractions were collected and kinase assays were performed on an aliquot of each fraction. The high molecular weight material (fractions 16–20) contained TNFα-inducible IκB kinase activity, which is specific for the WT substrate.

110 ml of S100 material (900 mg of protein; Bio-Rad Protein Assay) was pumped onto a Q-SEPHAROSE FAST FLOW column (56 ml bed volume, 2.6 cm ID) equilibrated at 2 ml/min with Buffer A containing 0.1% Brij-35. After the sample was loaded, the column was washed with 100 ml of Buffer A containing 0.1% Brij-35 and 100 mM NaCl, then a linear NaCl gradient was run from 100–300 mM. The gradient volume was 500 ml and the flow rate was 2 ml/min. Ten ml fractions were collected and the kinase assay was performed on those fractions that eluted during the gradient. Fractions corresponding to the TNFα-inducible IκB kinase activity (fractions 30–42, i.e. 20–32 of the gradient portion) were pooled. The pooled material contained 40 mg of protein.

The pooled material was diluted to 390 ml by addition of Buffer A containing 0.1 % Brij-35 and loaded onto a pre-equilibrated 5 ml HITRAP Q column (Pharmacia) at a flowrate of 4 ml/min. Following sample loading, the column was washed with 20 ml of Buffer A containing 0.1% Brij-35. The protein was eluted at 1 ml/min isocratically in Buffer A containing 0.1 % Brij-35 and 300 mM NaCl and 1 ml fractions were collected. Protein-containing fractions were identified using the BioRad assay and were collected and pooled to yield 4 ml of solution. Previously performed control experiments demonstrated that the kinase activity directly correlated with protein concentration.

The pooled material was diluted 1:1 with ATP column buffer (20 mM HEPES (pH 7.3), 50 mM β-GP, 60 mM $MgCl_2$, 1 mM $Na_2VO_4$, 1.5 mM EGTA, 1 mM DTT, 10 μg/ml aprotinin), then passed 4 times over a γ-ATP affinity column having 4 ml bed volume (Haystead et al., supra, 1993); the column had been prewashed with 2 M NaCl, 0.25% Brij-35 and equilibrated with 10 bed volumes of ATP column buffer containing 0.05% Brij-35 at a flow rate of 0.5 ml/min. Following loading of the sample, the column was washed with 10 ml of ATP column buffer containing 0.05% Brij-35, then with 10 ml ATP column buffer containing 0.05% Brij-35 and 250 mM NaCl.

Bound material was eluted in 10 ml of ATP column buffer containing 0.05% Brij-35, 250 mM NaCl and 10 mM ATP (elution buffer). Elution was performed by passing 5 ml of elution buffer through the column, allowing the column to incubate, capped, for 20 min, then passing an additional 5 ml of elution buffer through the column. The samples were pooled to yield 10 ml.

The 10 ml pooled sample from the ATP column was diluted with 30 ml Buffer A containing 0.1 % Brij-35 and loaded onto a 1 ml HITRAP Q column (Pharmacia) at 1 ml/min. The column was eluted at 0.4 ml/min with Buffer A containing 0.1% Brij-35 and 300 mM NaCl. 0.2 ml fractions were collected and the four protein-containing fractions were pooled (0.5 mg). The pooled material was concentrated to 200 µl on a 10K NANOSEP concentrator (Pall/Filtron) and loaded onto a SUPEROSE 6 gel filtration column (1.0×30 cm; Pharmacia). The SUPEROSE 6 column was equilibrated in Buffer A containing 0.1 % Brij-35 and 300 mM NaCl and run at a flowrate of 0.3 ml/min; 0.6 ml fractions were collected. Fractions 17, 18 and 19 contained kinase activity. Based on silver stained SDS-PAGE gels, the final purified material consisted of approximately 20 µg to 40 µg of total protein, of which approximately 2 µg corresponded to the 84 kDa IκB kinase band (catalytic subunit). The total time from the thawing of the S100 material until the collection of fractions from the gel filtration column was 24 hours.

C. Confirmation of IκB Kinase Purification:

Since the 84 kDa IκB kinase band identified by the kinase assay following the above procedure contained only about 10% of the total purified protein, three additional criteria were used to confirm that the identified band was an intrinsic component of the IκB kinase.

In one procedure, the elution profile of the SUPEROSE 6 column was analyzed by silver stained 8% SDS-PAGE gels, then compared to the kinase activity profile. For this analysis, 0.3 ml fractions were collected from the SUPEROSE 6 column, then separated by 8% SDS-PAGE and silver stained. This comparison confirmed that a single band of 84 kDa correlated precisely with the elution of IκB kinase activity.

In a second procedure, the IκB kinase was further purified on a substrate affinity column at 4° C. A GST fusion protein was prepared containing the A32/A36 1 to 54 amino acid sequence of IκBα repeated 8 times (GST-(8X-AA)). The GST-(8X-AA) then was covalently linked to a CNBr activated SEPHAROSE 4B resin to produce the substrate affinity resin.

IκB kinase-containing material was diluted into Buffer A to yield a final concentration of 70 mM NaCl, 0.025% Brij-35, then added to the substrate affinity resin at a ratio of 4:1 (solution:swollen beads). The resin was suspended and the mixture rotated gently overnight in a small column at 4° C. The resin was allowed to settle for 30 min, then the column was eluted by gravity. The column was washed with 4 bed volumes Buffer A containing 0.02% Brij-35, then the resin was suspended with 1.1 bed volumes of Buffer A containing 600 mM NaCl and 0.1 % Brij-35. The resin was allowed to settle for 40 min, then gravity elution was performed. The column was washed with an additional 1.1 bed volumes of Buffer A containing 600 mM NaCl and 0.1% Brij-35 and the two fractions were pooled.

The IκBα substrate affinity column was used for two separate experiments. In one experiment, the material that eluted from the final SUPEROSE 6 column was further purified on the IκBα substrate affinity column. In the second experiment, material obtained after the initial Q-SEPHAROSE column was purified on the IκBα substrate affinity column. The Q-SEPHAROSE bound fraction then was further purified on the ATP column and the SUPEROSE 6 column (see above).

Analysis of the purified material from these two experiments by silver stained SDS-PAGE gels revealed different protein profiles. However, comparison of these profiles revealed only two bands common to both preparations, one of which was confirmed to be the same 84 kDa band that was identified by the SUPEROSE 6 profile analysis and cofractionated with IκB kinase activity. The other band was 86 kDa in size. In several different experiments, the 84 kDa protein and 86 kDa protein were specifically purified by the substrate affinity column in what appeared to be an equimolar ratio.

In a third procedure, purified IκB kinase was treated with excess phosphatase, which inactivates the IκB kinase, then reactivated by addition of a semi-purified HeLa extract. Phosphatase inactivation was performed by adding excess protein phosphatase 2A catalytic domain (PP2A) to purified IκB kinase in 50 mM Tris (pH 7.6), 50 mM NaCl, 1 mM $MgCl_2$, then equilibrating the reaction for 60 min at 30° C. 1.25 µM okadaic acid was added to completely inactivate the phosphatase and the phosphatase inactivated material was used in standard kinase assays and to perform the reactivation and phosphorylation procedure.

Cytoplasmic extract was prepared using HeLa S3 cells. The cells were stimulated with TNFα for 5 min, then harvested in lysis buffer containing 0.1% NP-40 and 0.15 M NaCl. Reactivation was performed at 30° C. in kinase buffer for 60 min in the absence of $[\gamma^{-32}P]ATP$. Samples containing only cold ATP were used for kinase activity assays. Reactivation by the HeLa cell extract was performed in the presence of $[\gamma^{-32}P]ATP$, then the sample was separated by 8% SDS-PAGE and examined by autoradiography. A band of approximately 86 kDa was phosphorylated in the reactivated material and, associated with the reactivation procedure, was restoration of the IκB kinase activity.

D. Partial Amino Acid Sequence of IκB Kinase:

Following SDS-PAGE as described above, the 84 kDa band was excised from the gel and submitted for internal peptide sequencing analysis. Two peptide sequences were identified, as follows: KIIDLLPK (SEQ ID NO: 3) and KHR(D/A)LKPENIVLQDVG(P/G)K (SEQ ID NO: 4). Where a residue could not be unambiguously determined, an "X" was used to indicate no amino acid could be determined and parentheses were used to delimit amino acids that could not be distinguished. Since Lys-C protease was used to digest the protein, the presence of lysine residues at the N-termini of the peptides was inferred. Similarly, the 86 kDa band was excised and the sequences of proteolytic fragments was determined.

EXAMPLE II

Identification and Characterization of a Full Length Human IκB Kinase

This example provides methods for isolating the nucleic acid molecules encoding the IκB kinase and for characterizing the functional activity of the IκB kinase.

A. Cloning of cDNA Encoding Human IκB Kinase:

Degenerate oligonucleotide (length) sequences of the amino acid sequences of two peptide fragments (SEQ ID NOS: 3 and 4) of the IκB kinase protein (see FIG. 1) were searched in the GenBank DNA sequence database. This search revealed that nucleotide sequences encoding both peptide fragments were present in a partial cDNA encoding a portion of a protein designated human CHUK (GenBank Accession #U22512; Connelly and Marcu, supra, 1995).

Based on the human CHUK cDNA sequence, PCR primers were prepared corresponding to the 5'-terminus (5'-CCC CATATGTACCAGCATCGGGAA-3'; SEQ ID NO: 5) and 3'-terminus (3'-CCCCTCGAGTTCTGTTAACCAACT-5'; SEQ ID NO: 6). SEQ ID NO: 5 also contains a Nde I restriction endonuclease site (underlined) and an ATG (AUG) methionine codon (bold) and SEQ ID NO: 6 also contains an Xho I site. RNA was isolated from HeLa cells and first strand cDNA was prepared and used for a template by PCR using SEQ ID NOS: 5 and 6 as primers. The resulting 2.1 kilobase fragment was gel purified, $^{32}$P-labeled using oligo-dT and random primers, and used to screen a human fetal brain library (Clontech; Palo Alto Calif.) under high stringency conditions (50% formamide, 42° C.; Sambrook et al., supra, 1989).

In order to obtain the 5'-end of the cDNA encoding the IκB kinase, positive plaques from above were screened by PCR using two internal primers, (5'-CATGGCACCATCGTTCTCTG-3'; SEQ ID NO: 7), which is complementary to the sequence including the Ban I site around position 136 of SEQ ID NO: 1, and (5'-CTCAAAGAGCTCTGGGGCCAGATAC-3'; SEQ ID NO: 8), which is complementary to the sequence including the Sac I site around position 475, and a vector specific primer (TCCGAGATCTGGACGAGC-3'; SEQ ID NO: 9), which is complementary to vector sequences at the 5'-end of the cDNA insert. The longest PCR product was selected and sequenced by the dideoxy method.

DNA sequencing revealed that the cloned IκB kinase cDNA contained an additional 31 amino acids at the N-terminus as compared to human CHUK. The human IκB kinase shares a high amount of sequence identity with a protein designated mouse CHUK (GenBank Accession #U12473; Connelly and Marcu, supra, 1995). Although the mouse CHUK contains a domain having characteristics of a serine-threonine protein kinase, no functional activity of the protein was reported and no potential substrates were identified. The putative serine-threonine protein kinase domain of human CHUK was truncated at the N-terminus.

B. Expression of Human IκB Kinase or of an Antisense IκB Kinase Nucleic Acid in a Cell:

The full length IκB kinase cDNA and a cDNA encoding the Δ31 human CHUK protein (Connelly and Marcu, supra, 1995) were subcloned into the Nde I and Xho I sites of a bacterial expression vector encoding a carboxy terminal FLAG epitope and His-6 tag. Mammalian cell expression vectors were constructed by cleaving the bacterial expression vector with Nde I and Hind III, to release the cDNA inserts, converting the ends of the inserts to blunt ends using Klenow polymerase, and ligating the CDNA inserts encoding the full length IκB kinase or the Δ31 human CHUK into pCDNA3 (Invitrogen).

Alternatively, the IκB kinase CDNA and Δ31 cDNA were subcloned into the Bst XI site of the Rc/βactin vector (DiDonato et al., supra, 1996). Orientation of the inserts (sense or antisense) was determined by restriction endonuclease mapping and partial sequence using vector-specific primers. Vector containing the cDNA's inserted in the sense orientation were examined for expression of the encoded product by immunoblot analysis using an antibody specific for the FLAG epitope.

Transfection experiments were performed to determine the effect of expressing the cloned IκB kinase in HeLa cells or of expressing the cloned IκB kinase cDNA in the antisense orientation. One day prior to performing the transfections, HeLa cells were split into 35 mm dishes to approximately 50% confluency. Cells were transfected with 0.25 μg of a luciferase reporter gene containing an IL-8 promotor (Eckman et al., Amer. Soc. Clin. Invest. 96:1269–1279 (1995), which is incorporated herein by reference) along with either 1 μg pCDNA3 (Invitrogen, La Jolla Calif.; vector control), 1 μg pRCβactin-IκB-AA (sense orientation), 1 μg pRCβactin-IκB-K (antisense), or 0.1 μg pCDNA-IκB-K using the LIPOFECTAMINE method as recommended by the manufacturer (GIBCO/BRL, Gaithersburg Md.). Total DNA concentrations were kept constant by addition of empty pRCβactin DNA.

Transfected cells were incubated in DMEM containing 10% FBS for 24 hr. The cells then were washed and the growth medium was replaced with DMEM containing 0.1% FBS. Cells either were left untreated, or were treated with 20 ng/ml TNFα, 20 ng/ml IL-1α, or 100 ng/ml TPA (phorbol ester) for 3.5 hr. Cells were harvested by scraping and washed once with PBS, then lysed in 100 μl PBS containing 1% TRITON-X100. Luciferase assays were performed using 20 μl of lysate (DiDonato et al., supra, 1995). The protein concentration of each extract was determined using the BIORAD protein assay kit and luciferase activity was normalized according to the protein concentrations.

NF-κB is known to induce expression for the IL-8 promotor. Thus, as expected, treatment of the vector transfected control cells with TNFα, IL-1α or TPA resulted in a 3 to 5 fold increase in normalized luciferase activity. In comparison, in cells transfected with the cDNA encoding the IκB kinase, treatment with TNFα, IL-1α or TPA potentiated induction of luciferase activity 5 to 6 fold above the level of induction observed in the vector transfected cells. These results indicate that expression of the IκB kinase in cells increased the amount of NF-κB activated in response to the inducing agents.

In cells transfected with the vector expressing the antisense IκB kinase nucleic acid molecule, transcription of the luciferase reporter gene induced by IL-1 or TNFα was at the limit of detection, indicating transcription was almost completely inhibited due to expression of the antisense IκB kinase. This result indicates that the native IκB kinase is turned over relatively rapidly in the cells. Furthermore, treatment of the cells with the various inducing agents had no effect on the level of luciferase expression of control reporter genes, which are not responsive to NF-κB, as compared to the untreated cells. Other appropriate control experiments were performed in parallel. These results demonstrate the an expression of an antisense IκB kinase nucleic acid molecule in a cell can specifically inhibit NF-κB mediated gene expression.

EXAMPLE III

Use of IκB Kinase in a Drug Screening Assay

This example describes an assay for screening for agents such as drugs that alter the association of an IκB kinase and a second protein that specifically associates with the IκB kinase.

A GST-IκB kinase fusion protein or His-6-IκB kinase fusion protein can be prepared using methods as described above and purified using glutathione- or metal-chelation chromatography, respectively (Smith and Johnson, *Gene* 67:31–40 (1988), which is incorporated herein by reference). The fusion protein then is immobilized to a solid support taking advantage of the ability of the GST protein to specifically bind glutathione or of the His-6 peptide region to chelate a metal ion such as nickel (Ni) ion or cobalt (Co) ion (Clontech) by immobilized metal affinity chromatography. Alternatively, an anti-IκB kinase antibody can be immobilized on a matrix and the IκB kinase can be allowed to bind to the antibody.

The second protein, which can be IκB, for example, can be detectably labeled with a moiety such as a fluorescent molecule or a radiolabel (Hermanson, supra, 1996), then contacted in solution with the immobilized IκB kinase under conditions as described in Example I, which allow IκB to specifically associate with the IκB kinase. Preferably, the reactions are performed in 96 well plates, which allow automated reading of the reactions. Various agents such as drugs then are screened for the ability to alter the association of the IκB kinase and IκB.

The agent and labeled IκB can be added together to the immobilized IκB kinase, incubated to allow binding, then washed to remove unbound labeled IκB. The relative amount of binding of labeled IκB in the absence as compared to the presence of the agent being screened is determined by detecting the amount of label remaining in the plate. Appropriate controls are performed to account, for example, for nonspecific binding of the labeled IκB to the matrix. Such a method allows the identification of an agent that alter the association of an IκB kinase and a second protein such as IκB.

Alternatively, the labeled IκBcan be added to the immobilized IκB kinase and allowed to associate, then the agent can be added. Such a method allows the identification of agents that can induce the dissociation of a bound complex comprising the IκB kinase and IκB.

Although the invention has been described with reference to the examples provided above, it should be understood that various modifications can be made without departing from the spirit of the invention. Accordingly, the invention is limited only by the claims.

What is claimed is:

1. An isolated human protein kinase, which phosphorylates serine-32 and serine-36 of IκBα and which has an apparent molecular mass of 84 kiloDaltons as determined by SDS-polyacrylamide gel electrophoresis in an 8% gel under reducing conditions.

2. An isolated human protein kinase, which phosphorylates serine-32 and serine-36 of IκBα and which has an apparent molecular mass of 84 kiloDaltons as determined by SDS-polyacrylamide gel electrophoresis in an 8% gel under reducing conditions, comprising an amino acid sequence as shown in SEQ ID NO: 2.

3. A peptide portion of a polypeptide having the amino acid sequence shown in SEQ ID NO: 2, comprising at least six contiguous amino acids within positions 1 to 31 of SEQ ID NO: 2.

4. The peptide of claim 3, wherein one of said at least six contiguous amino acids further comprises the amino acid shown at position 30 or position 31 of SEQ ID NO: 2.

5. A method of obtaining the isolated IκB kinase of claim 1 from a sample containing the IκB kinase, comprising the steps of:

a) contacting the sample containing the IκB kinase with adenosine triphosphate (ATP) immobilized on a matrix, under conditions suitable for binding of said IκB kinase with said ATP;

b) obtaining the fraction of said sample that binds to said ATP, said fraction containing said IκB kinase;

c) contacting said fraction containing said IκB kinase with IκB immobilized on a matrix, under conditions suitable for binding of said IκB kinase with said IκB; and d) obtaining isolated IκB kinase from said IκB immobilized on a matrix.

6. The method of claim 5, wherein the sample containing the IκB kinase is a cell sample stimulated with TNFα.

7. A peptide portion of a polypeptide having the amino acid sequence shown in SEQ ID NO: 2, comprising at least ten contiguous amino acids within positions 1 to 31 of SEQ ID NO: 2.

8. The peptide of claim 3, wherein one of said at least ten contiguous amino acids further comprises the amino acid shown at position 30 or position 31 of SEQ ID NO: 2.

* * * * *

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
        (A) LENGTH: 2273 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 36..2271

(xi) SEQUENCE DESCRIPTION: SEQ ID NO:1:

```
TCGACGGAAC CTGAGGCCGC TTGCCCTCCC GCCCC ATG GAG CGG CCC CCG GGG           53
                                      Met Glu Arg Pro Pro Gly
                                        1               5

CTG CGG CCG GGC GCG GGC GGG CCC TGG GAG ATG CGG GAG CGG CTG GGC         101
Leu Arg Pro Gly Ala Gly Gly Pro Trp Glu Met Arg Glu Arg Leu Gly
            10                  15                  20

ACC GGC GGC TTC GGG AAC GTC TGT CTG TAC CAG CAT CGG GAA CTT GAT         149
Thr Gly Gly Phe Gly Asn Val Cys Leu Tyr Gln His Arg Glu Leu Asp
        25                  30                  35

CTC AAA ATA GCA ATT AAG TCT TGT CGC CTA GAG CTA AGT ACC AAA AAC         197
Leu Lys Ile Ala Ile Lys Ser Cys Arg Leu Glu Leu Ser Thr Lys Asn
    40                  45                  50

AGA GAA CGA TGG TGC CAT GAA ATC CAG ATT ATG AAG AAG TTG AAC CAT         245
Arg Glu Arg Trp Cys His Glu Ile Gln Ile Met Lys Lys Leu Asn His
55                  60                  65                  70

GCC AAT GTT GTA AAG GCC TGT GAT GTT CCT GAA GAA TTG AAT ATT TTG         293
Ala Asn Val Val Lys Ala Cys Asp Val Pro Glu Glu Leu Asn Ile Leu
                75                  80                  85

ATT CAT GAT GTG CCT CTT CTA GCA ATG GAA TAC TGT TCT GGA GGA GAT         341
Ile His Asp Val Pro Leu Leu Ala Met Glu Tyr Cys Ser Gly Gly Asp
            90                  95                 100

CTC CGA AAG CTG CTC AAC AAA CCA GAA AAT TGT TGT GGA CTT AAA GAA         389
Leu Arg Lys Leu Leu Asn Lys Pro Glu Asn Cys Cys Gly Leu Lys Glu
        105                 110                 115

AGC CAG ATA CTT TCT TTA CTA AGT GAT ATA GGG TCT GGG ATT CGA TAT         437
Ser Gln Ile Leu Ser Leu Leu Ser Asp Ile Gly Ser Gly Ile Arg Tyr
    120                 125                 130

TTG CAT GAA AAC AAA ATT ATA CAT CGA GAT CTA AAA CCT GAA AAC ATA         485
Leu His Glu Asn Lys Ile Ile His Arg Asp Leu Lys Pro Glu Asn Ile
135                 140                 145                 150
```

-continued

```
GTT CTT CAG GAT GTT GGT GGA AAG ATA ATA CAT AAA ATA ATT GAT CTG      533
Val Leu Gln Asp Val Gly Gly Lys Ile Ile His Lys Ile Ile Asp Leu
                155                 160                 165

GGA TAT GCC AAA GAT GTT GAT CAA GGA AGT CTG TGT ACA TCT TTT GTG      581
Gly Tyr Ala Lys Asp Val Asp Gln Gly Ser Leu Cys Thr Ser Phe Val
            170                 175                 180

GGA ACA CTG CAG TAT CTG GCC CCA GAG CTC TTT GAG AAT AAG CCT TAC      629
Gly Thr Leu Gln Tyr Leu Ala Pro Glu Leu Phe Glu Asn Lys Pro Tyr
        185                 190                 195

ACA GCC ACT GTT GAT TAT TGG AGC TTT GGG ACC ATG GTA TTT GAA TGT      677
Thr Ala Thr Val Asp Tyr Trp Ser Phe Gly Thr Met Val Phe Glu Cys
    200                 205                 210

ATT GCT GGA TAT AGG CCT TTT TTG CAT CAT CTG CAG CCA TTT ACC TGG      725
Ile Ala Gly Tyr Arg Pro Phe Leu His His Leu Gln Pro Phe Thr Trp
215                 220                 225                 230

CAT GAG AAG ATT AAG AAG AAG GAT CCA AAG TGT ATA TTT GCA TGT GAA      773
His Glu Lys Ile Lys Lys Lys Asp Pro Lys Cys Ile Phe Ala Cys Glu
                235                 240                 245

GAG ATG TCA GGA GAA GTT CGG TTT AGT AGC CAT TTA CCT CAA CCA AAT      821
Glu Met Ser Gly Glu Val Arg Phe Ser Ser His Leu Pro Gln Pro Asn
            250                 255                 260

AGC CTT TGT AGT TTA ATA GTA GAA CCC ATG GAA AAC TGG CTA CAG TTG      869
Ser Leu Cys Ser Leu Ile Val Glu Pro Met Glu Asn Trp Leu Gln Leu
        265                 270                 275

ATG TTG AAT TGG GAC CCT CAG CAG AGA GGA GGA CCT GTT GAC CTT ACT      917
Met Leu Asn Trp Asp Pro Gln Gln Arg Gly Gly Pro Val Asp Leu Thr
    280                 285                 290

TTG AAG CAG CCA AGA TGT TTT GTA TTA ATG GAT CAC ATT TTG AAT TTG      965
Leu Lys Gln Pro Arg Cys Phe Val Leu Met Asp His Ile Leu Asn Leu
295                 300                 305                 310

AAG ATA GTA CAC ATC CTA AAT ATG ACT TCT GCA AAG ATA ATT TCT TTT     1013
Lys Ile Val His Ile Leu Asn Met Thr Ser Ala Lys Ile Ile Ser Phe
                315                 320                 325

CTG TTA CCA CCT GAT GAA AGT CTT CAT TCA CTA CAG TCT CGT ATT GAG     1061
Leu Leu Pro Pro Asp Glu Ser Leu His Ser Leu Gln Ser Arg Ile Glu
            330                 335                 340

CGT GAA ACT GGA ATA AAT ACT GGT TCT CAA GAA CTT CTT TCA GAG ACA     1109
Arg Glu Thr Gly Ile Asn Thr Gly Ser Gln Glu Leu Leu Ser Glu Thr
        345                 350                 355

GGA ATT TCT CTG GAT CCT CGG AAA CCA GCC TCT CAA TGT GTT CTA GAT     1157
Gly Ile Ser Leu Asp Pro Arg Lys Pro Ala Ser Gln Cys Val Leu Asp
    360                 365                 370

GGA GTT AGA GGC TGT GAT AGC TAT ATG GTT TAT TTG TTT GAT AAA AGT     1205
Gly Val Arg Gly Cys Asp Ser Tyr Met Val Tyr Leu Phe Asp Lys Ser
375                 380                 385                 390

AAA ACT GTA TAT GAA GGG CCA TTT GCT TCC AGA AGT TTA TCT GAT TGT     1253
Lys Thr Val Tyr Glu Gly Pro Phe Ala Ser Arg Ser Leu Ser Asp Cys
                395                 400                 405

GTA AAT TAT ATT GTA CAG GAC AGC AAA ATA CAG CTT CCA ATT ATA CAG     1301
Val Asn Tyr Ile Val Gln Asp Ser Lys Ile Gln Leu Pro Ile Ile Gln
            410                 415                 420

CTG CGT AAA GTG TGG GCT GAA GCA GTG CAC TAT GTG TCT GGA CTA AAA     1349
Leu Arg Lys Val Trp Ala Glu Ala Val His Tyr Val Ser Gly Leu Lys
        425                 430                 435

GAA GAC TAT AGC AGG CTC TTT CAG GGA CAA AGG GCA GCA ATG TTA AGT     1397
Glu Asp Tyr Ser Arg Leu Phe Gln Gly Gln Arg Ala Ala Met Leu Ser
    440                 445                 450

CTT CTT AGA TAT AAT GCT AAC TTA ACA AAA ATG AAG AAC ACT TTG ATC     1445
Leu Leu Arg Tyr Asn Ala Asn Leu Thr Lys Met Lys Asn Thr Leu Ile
```

```
455                460                465                470
TCA GCA TCA CAA CAA CTG AAA GCT AAA TTG GAG TTT TTT CAC AAA AGC    1493
Ser Ala Ser Gln Gln Leu Lys Ala Lys Leu Glu Phe Phe His Lys Ser
            475                480                485

ATT CAG CTT GAC TTG GAG AGA TAC AGC GAG CAG ATG ACG TAT GGG ATA    1541
Ile Gln Leu Asp Leu Glu Arg Tyr Ser Glu Gln Met Thr Tyr Gly Ile
            490                495                500

TCT TCA GAA AAA ATG CTA AAA GCA TGG AAA GAA ATG GAA GAA AAG GCC    1589
Ser Ser Glu Lys Met Leu Lys Ala Trp Lys Glu Met Glu Glu Lys Ala
            505                510                515

ATC CAC TAT GCT GAG GTT GGT GTC ATT GGA TAC CTG GAG GAT CAG ATT    1637
Ile His Tyr Ala Glu Val Gly Val Ile Gly Tyr Leu Glu Asp Gln Ile
            520                525                530

ATG TCT TTG CAT GCT GAA ATC ATG GAG CTA CAG AAG AGC CCC TAT GGA    1685
Met Ser Leu His Ala Glu Ile Met Glu Leu Gln Lys Ser Pro Tyr Gly
535                540                545                550

AGA CGT CAG GGA GAC TTG ATG GAA TCT CTG GAA CAG CGT GCC ATT GAT    1733
Arg Arg Gln Gly Asp Leu Met Glu Ser Leu Glu Gln Arg Ala Ile Asp
            555                560                565

CTA TAT AAG CAG TTA AAA CAC AGA CCT TCA GAT CAC TCC TAC AGT GAC    1781
Leu Tyr Lys Gln Leu Lys His Arg Pro Ser Asp His Ser Tyr Ser Asp
            570                575                580

AGC ACA GAG ATG GTG AAA ATC ATT GTG CAC ACT GTG CAG AGT CAG GAC    1829
Ser Thr Glu Met Val Lys Ile Ile Val His Thr Val Gln Ser Gln Asp
            585                590                595

CGT GTG CTC AAG GAG CGT TTT GGT CAT TTG AGC AAG TTG TTG GGC TGT    1877
Arg Val Leu Lys Glu Arg Phe Gly His Leu Ser Lys Leu Leu Gly Cys
            600                605                610

AAG CAG AAG ATT ATT GAT CTA CTC CCT AAG GTG GAA GTG GCC CTC AGT    1925
Lys Gln Lys Ile Ile Asp Leu Leu Pro Lys Val Glu Val Ala Leu Ser
615                620                625                630

AAT ATC AAA GAA GCT GAC AAT ACT GTC ATG TTC ATG CAG GGA AAA AGG    1973
Asn Ile Lys Glu Ala Asp Asn Thr Val Met Phe Met Gln Gly Lys Arg
            635                640                645

CAG AAA GAA ATA TGG CAT CTC CTT AAA ATT GCC TGT ACA CAG AGT TCT    2021
Gln Lys Glu Ile Trp His Leu Leu Lys Ile Ala Cys Thr Gln Ser Ser
            650                655                660

GCC CGC TCT CTT GTA GGA TCC AGT CTA GAA GGT GCA GTA ACC CCT CAA    2069
Ala Arg Ser Leu Val Gly Ser Ser Leu Glu Gly Ala Val Thr Pro Gln
            665                670                675

GCA TAC GCA TGG CTG GCC CCC GAC TTA GCA GAA CAT GAT CAT TCT CTG    2117
Ala Tyr Ala Trp Leu Ala Pro Asp Leu Ala Glu His Asp His Ser Leu
            680                685                690

TCA TGT GTG GTA ACT CCT CAA GAT GGG GAG ACT TCA GCA CAA ATG ATA    2165
Ser Cys Val Val Thr Pro Gln Asp Gly Glu Thr Ser Ala Gln Met Ile
695                700                705                710

GAA GAA AAT TTG AAC TGC CTT GGC CAT TTA AGC ACT ATT ATT CAT GAG    2213
Glu Glu Asn Leu Asn Cys Leu Gly His Leu Ser Thr Ile Ile His Glu
            715                720                725

GCA AAT GAG GAA CAG GGC AAT AGT ATG ATG AAT CTT GAT TGG AGT TGG    2261
Ala Asn Glu Glu Gln Gly Asn Ser Met Met Asn Leu Asp Trp Ser Trp
            730                735                740

TTA ACA GAA T GA                                                    2273
Leu Thr Glu
        745
```

(2) INFORMATION FOR SEQ ID NO:2:

(i) SEQUENCE CHARACTERISTICS:
        (A) LENGTH: 745 amino acids (B) TYPE: amino acid
    (D) TOPOLOGY: linear (ii) MOLECULE TYPE: protein (xi) SEQUENCE DESCRIPTION: SEQ ID NO:2:

```
Met Glu Arg Pro Pro Gly Leu Arg Pro Gly Ala Gly Gly Pro Trp Glu
 1               5                  10                  15

Met Arg Glu Arg Leu Gly Thr Gly Gly Phe Gly Asn Val Cys Leu Tyr
                20                  25                  30

Gln His Arg Glu Leu Asp Leu Lys Ile Ala Ile Lys Ser Cys Arg Leu
            35                  40                  45

Glu Leu Ser Thr Lys Asn Arg Glu Arg Trp Cys His Glu Ile Gln Ile
        50                  55                  60

Met Lys Lys Leu Asn His Ala Asn Val Val Lys Ala Cys Asp Val Pro
 65                 70                  75                  80

Glu Glu Leu Asn Ile Leu Ile His Asp Val Pro Leu Leu Ala Met Glu
                85                  90                  95

Tyr Cys Ser Gly Gly Asp Leu Arg Lys Leu Leu Asn Lys Pro Glu Asn
                100                 105                 110

Cys Cys Gly Leu Lys Glu Ser Gln Ile Leu Ser Leu Leu Ser Asp Ile
            115                 120                 125

Gly Ser Gly Ile Arg Tyr Leu His Glu Asn Lys Ile Ile His Arg Asp
        130                 135                 140

Leu Lys Pro Glu Asn Ile Val Leu Gln Asp Val Gly Gly Lys Ile Ile
145                 150                 155                 160

His Lys Ile Ile Asp Leu Gly Tyr Ala Lys Asp Val Asp Gln Gly Ser
                165                 170                 175

Leu Cys Thr Ser Phe Val Gly Thr Leu Gln Tyr Leu Ala Pro Glu Leu
            180                 185                 190

Phe Glu Asn Lys Pro Tyr Thr Ala Thr Val Asp Tyr Trp Ser Phe Gly
        195                 200                 205

Thr Met Val Phe Glu Cys Ile Ala Gly Tyr Arg Pro Phe Leu His His
    210                 215                 220

Leu Gln Pro Phe Thr Trp His Glu Lys Ile Lys Lys Lys Asp Pro Lys
225                 230                 235                 240

Cys Ile Phe Ala Cys Glu Glu Met Ser Gly Glu Val Arg Phe Ser Ser
                245                 250                 255

His Leu Pro Gln Pro Asn Ser Leu Cys Ser Leu Ile Val Glu Pro Met
            260                 265                 270

Glu Asn Trp Leu Gln Leu Met Leu Asn Trp Asp Pro Gln Gln Arg Gly
        275                 280                 285

Gly Pro Val Asp Leu Thr Leu Lys Gln Pro Arg Cys Phe Val Leu Met
    290                 295                 300

Asp His Ile Leu Asn Leu Lys Ile Val His Ile Leu Asn Met Thr Ser
305                 310                 315                 320

Ala Lys Ile Ile Ser Phe Leu Leu Pro Pro Asp Glu Ser Leu His Ser
                325                 330                 335

Leu Gln Ser Arg Ile Glu Arg Glu Thr Gly Ile Asn Thr Gly Ser Gln
            340                 345                 350

Glu Leu Leu Ser Glu Thr Gly Ile Ser Leu Asp Pro Arg Lys Pro Ala
        355                 360                 365

Ser Gln Cys Val Leu Asp Gly Val Arg Gly Cys Asp Ser Tyr Met Val
    370                 375                 380
```

```
Tyr Leu Phe Asp Lys Ser Lys Thr Val Tyr Glu Gly Pro Phe Ala Ser
385                 390                 395                 400

Arg Ser Leu Ser Asp Cys Val Asn Tyr Ile Val Gln Asp Ser Lys Ile
            405                 410                 415

Gln Leu Pro Ile Ile Gln Leu Arg Lys Val Trp Ala Glu Ala Val His
            420                 425                 430

Tyr Val Ser Gly Leu Lys Glu Asp Tyr Ser Arg Leu Phe Gln Gly Gln
            435                 440                 445

Arg Ala Ala Met Leu Ser Leu Leu Arg Tyr Asn Ala Asn Leu Thr Lys
450                 455                 460

Met Lys Asn Thr Leu Ile Ser Ala Ser Gln Gln Leu Lys Ala Lys Leu
465                 470                 475                 480

Glu Phe Phe His Lys Ser Ile Gln Leu Asp Leu Glu Arg Tyr Ser Glu
            485                 490                 495

Gln Met Thr Tyr Gly Ile Ser Ser Glu Lys Met Leu Lys Ala Trp Lys
            500                 505                 510

Glu Met Glu Glu Lys Ala Ile His Tyr Ala Glu Val Gly Val Ile Gly
            515                 520                 525

Tyr Leu Glu Asp Gln Ile Met Ser Leu His Ala Glu Ile Met Glu Leu
530                 535                 540

Gln Lys Ser Pro Tyr Gly Arg Arg Gln Gly Asp Leu Met Glu Ser Leu
545                 550                 555                 560

Glu Gln Arg Ala Ile Asp Leu Tyr Lys Gln Leu Lys His Arg Pro Ser
            565                 570                 575

Asp His Ser Tyr Ser Asp Ser Thr Glu Met Val Lys Ile Ile Val His
            580                 585                 590

Thr Val Gln Ser Gln Asp Arg Val Leu Lys Glu Arg Phe Gly His Leu
            595                 600                 605

Ser Lys Leu Leu Gly Cys Lys Gln Lys Ile Ile Asp Leu Leu Pro Lys
            610                 615                 620

Val Glu Val Ala Leu Ser Asn Ile Lys Glu Ala Asp Asn Thr Val Met
625                 630                 635                 640

Phe Met Gln Gly Lys Arg Gln Lys Glu Ile Trp His Leu Leu Lys Ile
            645                 650                 655

Ala Cys Thr Gln Ser Ser Ala Arg Ser Leu Val Gly Ser Ser Leu Glu
            660                 665                 670

Gly Ala Val Thr Pro Gln Ala Tyr Ala Trp Leu Ala Pro Asp Leu Ala
            675                 680                 685

Glu His Asp His Ser Leu Ser Cys Val Val Thr Pro Gln Asp Gly Glu
690                 695                 700

Thr Ser Ala Gln Met Ile Glu Glu Asn Leu Asn Cys Leu Gly His Leu
705                 710                 715                 720

Ser Thr Ile Ile His Glu Ala Asn Glu Glu Gln Gly Asn Ser Met Met
            725                 730                 735

Asn Leu Asp Trp Ser Trp Leu Thr Glu
            740                 745

(2) INFORMATION FOR SEQ ID NO:3:

(i) SEQUENCE CHARACTERISTICS:
        (A) LENGTH: 8 amino acids
        (B) TYPE: amino acid
        (D) TOPOLOGY: linear (ii) MOLECULE TYPE: peptide
```

(xi) SEQUENCE DESCRIPTION: SEQ ID NO:3:

Lys Ile Ile Asp Leu Leu Pro Lys
1               5

(2) INFORMATION FOR SEQ ID NO:4:

(i) SEQUENCE CHARACTERISTICS:
            (A) LENGTH: 18 amino acids
            (B) TYPE: amino acid
            (D) TOPOLOGY: linear (ii) MOLECULE TYPE: peptide (ix) FEATURE:
            (A) NAME/KEY: Peptide
            (B) LOCATION: 4
            (D) OTHER INFORMATION: /note= "Xaa is aspartic acid or
                alanine (D/A)."

(ix) FEATURE:
            (A) NAME/KEY: Peptide
            (B) LOCATION: 17
            (D) OTHER INFORMATION: /note= "Xaa is proline or glycine
                (P/G)."

(xi) SEQUENCE DESCRIPTION: SEQ ID NO:4:

Lys His Arg Xaa Leu Lys Pro Glu Asn Ile Val Leu Gln Asp Val Gly
1               5                   10                  15

Xaa Lys (2) INFORMATION FOR SEQ ID NO:5:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (xi) SEQUENCE DESCRIPTION: SEQ ID NO:5:

CCCCATATGT ACCAGCATCG GGAA                                              24

(2) INFORMATION FOR SEQ ID NO:6:

(i) SEQUENCE CHARACTERISTICS:
            (A) LENGTH: 24 amino acids
            (B) TYPE: amino acid
            (C) STRANDEDNESS: single
            (D) TOPOLOGY: linear (xi) SEQUENCE DESCRIPTION: SEQ ID NO:6:

Thr Cys Ala Ala Cys Cys Ala Ala Thr Thr Gly Thr Cys Thr Thr Gly
1               5                   10                  15

Ala Gly Cys Thr Cys Cys Cys Cys
                20

(2) INFORMATION FOR SEQ ID NO:7:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:7:

CATGGCACCA TCGTTCTCTG                                                   20

(2) INFORMATION FOR SEQ ID NO:8:

(i) SEQUENCE CHARACTERISTICS:
    (A) LENGTH: 25 base pairs
    (B) TYPE: nucleic acid
    (C) STRANDEDNESS: single
    (D) TOPOLOGY: linear (xi) SEQUENCE DESCRIPTION: SEQ ID NO:8:

CTCAAAGAGC TCTGGGGCCA GATAC                     25

(2) INFORMATION FOR SEQ ID NO:9:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:9:

TCCGAGATCT GGACGAGC                             18